(12) United States Patent
Palsson

(10) Patent No.: US 8,606,553 B2
(45) Date of Patent: *Dec. 10, 2013

(54) METHODS FOR IDENTIFYING DRUG TARGETS BASED ON GENOMIC SEQUENCE DATA

(75) Inventor: Bernhard Palsson, La Jolla, CA (US)

(73) Assignee: The Regents of the University of California, Oakland, CA (US)

( * ) Notice: Subject to any disclaimer, the term of this patent is extended or adjusted under 35 U.S.C. 154(b) by 366 days.

This patent is subject to a terminal disclaimer.

(21) Appl. No.: 09/923,870

(22) Filed: Aug. 6, 2001

(65) Prior Publication Data

US 2002/0012939 A1     Jan. 31, 2002

Related U.S. Application Data

(63) Continuation of application No. 09/243,022, filed on Feb. 2, 1999, now abandoned.

(51) Int. Cl.
    *G06G 7/56*     (2006.01)
    *G01N 33/48*     (2006.01)
    *G01N 31/00*     (2006.01)
    *G06F 19/12*     (2011.01)

(52) U.S. Cl.
    CPC ........................... *G06F 19/12* (2013.01)
    USPC .................. 703/5; 702/19; 702/27

(58) Field of Classification Search
    USPC ................... 435/6, 34; 702/19, 20
    See application file for complete search history.

(56) References Cited

U.S. PATENT DOCUMENTS

| | | |
|---|---|---|
| 5,273,038 A | 12/1993 | Beavin et al. |
| 5,556,762 A | 9/1996 | Pinilla et al. |
| 5,639,949 A | 6/1997 | Ligon et al. |
| 5,689,633 A | 11/1997 | Cotner et al. |
| 5,914,891 A | 6/1999 | McAdams et al. |
| 5,930,154 A | 7/1999 | Thalhammer-Reyero |
| 5,947,899 A | 9/1999 | Winslow et al. |
| 5,980,096 A | 11/1999 | Thalhammer-Reyero |
| 6,132,969 A | 10/2000 | Stoughton et al. |
| 6,165,709 A | 12/2000 | Friend et al. |
| 6,200,803 B1 | 3/2001 | Roberts |
| 6,221,597 B1 | 4/2001 | Roberts |

(Continued)

FOREIGN PATENT DOCUMENTS

| | | |
|---|---|---|
| WO | WO 92/09300 | 6/1992 |
| WO | WO 00/46405 | 8/2000 |

(Continued)

OTHER PUBLICATIONS

Edwards et al., Journal of Biological Chemistry, 274(25):17410-17416, Jun. 18, 1999.*

(Continued)

*Primary Examiner* — Russell S Negin
(74) *Attorney, Agent, or Firm* — Jones Day

(57) ABSTRACT

This invention provides a computational approach to identifying potential antibacterial drug targets based on a genome sequence and its annotation. Starting from a fully sequenced genome, open reading frame assignments are made which determine the metabolic genotype for the organism. The metabolic genotype, and more specifically its stoichiometric matrix, are analyzed using flux balance analysis to assess the effects of genetic deletions on the fitness of the organism and its ability to produce essential biomolecules required for growth.

26 Claims, 3 Drawing Sheets

(56) References Cited

U.S. PATENT DOCUMENTS

| | | | |
|---|---|---|---|
| 6,302,302 | B1 | 10/2001 | Albisetti |
| 6,326,140 | B1 | 12/2001 | Rine et al. |
| 6,329,139 | B1 | 12/2001 | Nova et al. |
| 6,351,712 | B1 | 2/2002 | Stoughton et al. |
| 6,370,478 | B1 | 4/2002 | Stoughton et al. |
| 6,379,964 | B1 | 4/2002 | Del Cardayre et al. |
| 6,500,710 | B2 | 12/2002 | Nakagawa |
| 6,902,692 | B2 | 6/2005 | Carper |
| 6,983,227 | B1 | 1/2006 | Thalhammer-Reyero |
| 7,127,379 | B2 | 10/2006 | Palsson et al. |
| 2002/0012939 | A1 | 1/2002 | Palsson et al. |
| 2002/0051998 | A1 | 5/2002 | Schmidt-Dannert et al. |
| 2002/0168654 | A1 | 11/2002 | Maranas et al. |
| 2003/0059792 | A1 | 3/2003 | Palsson et al. |
| 2003/0113761 | A1 | 6/2003 | Tan et al. |
| 2003/0224363 | A1 | 12/2003 | Park et al. |
| 2003/0233218 | A1 | 12/2003 | Schilling |
| 2004/0009466 | A1 | 1/2004 | Maranas et al. |
| 2004/0029149 | A1 | 2/2004 | Palsson et al. |
| 2004/0072723 | A1 | 4/2004 | Palsson et al. |
| 2006/0147899 | A1 | 7/2006 | Famili et al. |
| 2007/0111294 | A1 | 5/2007 | Burgard et al. |
| 2008/0176327 | A1 | 7/2008 | Palsson et al. |

FOREIGN PATENT DOCUMENTS

| | | |
|---|---|---|
| WO | WO 01/36658 | 5/2001 |
| WO | WO 01/57775 | 8/2001 |
| WO | WO 02/055995 | 7/2002 |
| WO | WO 01/61115 | 8/2002 |
| WO | WO 03/106998 | 12/2003 |

OTHER PUBLICATIONS

Stryer, L., Biochemistry ($2^{nd}$ Edition), W.H. Freeman and Company, San Francisco, 1981, p. 288.*

Edwards et al., Genomically Based Comparative Flux Balance Analysis of *Escherichia coli* and *Haemophilus influenzae*, Abstracts of Papers, American Chemical Society, 213(1-3): BIOT 50, San Francisco, Apr. 13-17, 1997.*

Pennisi, Laboratory Workhorse Decoded, Science, 277:1432-1434, Sep. 1997.*

Kunst et al. The project of sequencing the entire *Bacillus substilis* genome. Research in Microbiology. 1991, vol. 142, pp. 905-912.*

Five pages from URL: web.archive.org/web/20050731094028/ http://www.chem.qmw.ac.uk/iubmb/enzyme/ Enzyme Nomenclature database maintained by G. P. Moss of Queen Mary and Westfield Colege in the United Kingdom; Date Obtained May 15, 2009.*

Three pages from URL: web.archive.org/web/19981206132808/ http://ecocyc.panbio.com/ecocyc/ecocyc.html; Ecocyc; obtained on Sep. 18, 2009.*

Three pages from URL: web.archive.org/web/2007001095540/ http://mips.gsf.de/proj/yeast/pathways on Jun. 6, 2008. MIPS, website: Comprehensive Yeast Genome Database—Pathways; Date Obtained Sep. 18, 2009.*

Two pages from URL: www.ncbi.nlm.nih.gov/sites/ entrz?db=genome obtained on Jun. 15, 2009.*

Six pages from URL: web.archive.org/web/2005025215224/ genome-www.stanford.edu/~sherlock/cluster.html, "XCluster" software; obtained on Sep. 18, 2009.*

Two pages from URL: web.archive.org/web/20060712190022/ http://www.tigr.org/. The Institute for Genome Research, J. Craig Venter Institute; obtained on Sep. 18, 2009.*

Home page from URL: web.archive.org/web/20021126044821/ http://tula.cifn.unam.mx:8850/regulondb/regulon_intro.frameset; obtained on Sep. 18, 2009.*

Home page from URL: web.archive.org/web/20041125063300/ http://wit.acs.ani.org; What is There (WIT), Obtained Nov. 23, 2008.*

Home page from URL: web.archive.org/web/20050201083239/ igweb.integratedgenomics.com/MPW/, Metabolic pathways database (MPW), obtained on Sep. 18, 2009.*

Home page from URL: web.archive.org/web/20070228190312/ http://systemsbiology.ucsd.edu, obtained on Sep. 18, 2009.*

Arigoni, et al., *A Genome-Based Approach for the Identification of Essential Bacterial Genes*: Nature Biotechnology, US. Nature Publishing: vol. 16:9 (1998).

Baltz, et al., *DNA Sequence Sampling of the Streptococcus pneumonia genome to identify novel targets for antibiotic development*: Microbial Drug Resistant US. Liebert vol. 4, No. 1:1-9 (1998).

Blattner, Frederick, *The Complete Genome Sequence of Escherichia coli K-12*. Science. vol. 2777, pp. 1453-1462, Sep. 1997.

Bonarius, Hendrik, *Flux Analysis of Underdetermined metabolic networks: the quest for the missing constraints*. Tibtech, vol. 15, pp. 308-324, Aug. 1997.

Edwards, Jeremy, et al. *How Will Bioinformatics Influence Metabolic Engineering* Biotechnology & Bioengineering, vol. 58, No. 2-3:162-69 (1998).

Everett, et al., *Pendred syndrome is caused by mutations in a putative sulphate transporter gene (PDS)*. Nature Genetics vol. 17, pp. 411-422 (1997).

Fell, David. *Fat Synthesis in Adipose Tissue*. J. Brochen, vol. 238, pp. 781-786 (1986).

Earp, et al. *Ecoye Encyclopedia of Escherichia coli Genes and Metabolism*: Nucleic Acids Research, vol. 25, No. 1:43-50 (1997).

Earp, P.D., *Metabolic databases*:TIBS Trends in Biochemical Science, en. Elsevier Publication. Cambridge: vol. 23, No. 3:114-115 (1998).

Majewski, R A. *Simple Constrained Optimization View of Acetate Overflow in E. coli*. Biotechnology and Bioengineering, vol. 35, pp. 732-738 (1990).

Palsson, B., *What lies Beyond Bioinformatics* Nature Biotechnology vol. 15:3-4 (1997).

Pramanik et al., *Stoichiometric model of Escherichia coli metabolism: Incorporation of growth rate dependent biomass composition and mechanistic energy requierements*, Biotechnology and Bioengineering, vol. 56, No. 4:398-421 (1997).

Sauer, et al., *Metabolic Capacity of Bacillus subtilis for the Production of Purine Nucleosides, Riboflavin, and Folic Acid* Biotechnology and Bioengineering, vol. 59, No. 2:227-238 (1998).

Schilling, et al., *Toward Metobolic Phenomics: Analysis and Genomic Data Using Flax Balances* Biotechnology Progress vol. 15, No. 3:288-95 (1999).

Scott, et al., *The Pendred syndrome gene encodes a chloride-iodide transport protein*. Nature Genetics, vol. 21, pp. 44-443 (1999).

Tomita, et al., *E-Cell: Software Environment for Whole-Cell Simulation*: Bioinformatics, vol. 15, No. 1: 72-84 (1999).

Varma, Amit, *Metabolic Flux Balancing: Basic Concepts, Scientific and Practical Use*. Bio Technology vol. 12, pp. 994-998, Oct. 1994.

Xie, et al., *Integrated Approaches to the Design of Media and Feeding Strategies For Fed-Batch Cultures of Animal Cells*: Trends in Biotechnology, GB, Elsevier Publications Cambridge: vol. 15, No. 3:109-113 (1997).

Galperin and Brenner; Using Metabolic Pathway Databases for Functional Annotation, pp. 332-333, Trends in Genetics, vol. 14: No. 8 (Aug. 1998).

Adamowicz, et al., "Nutritional complementation of oxidative glucose metabolism in *Escherichia coli* via pyrroloquinoline quinone-dependent glucose dehydrogenase and the Entner-Doudoroff pathway," *Appl Environ Microbiol*, 57(7):2012-2015 (1991).

Alberty, "Calculation of Biochemical Net Reactions and Pathways by Using Matrix Operations," *Biophys J*, 71(1):507-515 (1996).

Alm, et al., "Genomic-sequence comparison of two unrelated isolates of the human gastric pathogen *Helicobacter pylori*," *Nature*, 397(6715):176-80 (1999).

Alon, et al., "Broad patterns of gene expression revealed by clustering analysis of tumor and normal colon tissues probed by oligonucleotide arrays," *Proc Natl Acad Sci U.S.A.*, 96(12):6745-6750 (1999).

Alter, et al., "Singular value decomposition for genome-wide expression data processing and modeling," *Proc Natl Acad Sci U.S.A.*, 97(18):10101-10106 (2000).

Altschul, et al., "Gapped BLAST and PSI-BLAST: A New Generation of Protein Database Search Programs," *Nucl Acids Res*, 25(17):3389-3402 (1997).

(56) References Cited

OTHER PUBLICATIONS

Alves, et al., "Systemic properties of ensembles of metabolic networks: application of graphical and statistical methods to simple unbranched pathways," *Bioinformatics*, 16(6):534-547 (2000).
Andre, "An overview of membrane transport proteins in *Saccharomyces cerevisiae*," *Yeast*, 11(16):1575-1611 (1995).
Anonymous, "The yeast genome directory" *Nature*, 387(6632 Suppl):5 (1997).
Appel, et al., "A new generation of information retrieval tools for biologists: the example of the ExPASy WWW server," *Trends Biochem Sci*, 19(6):258-260 (1994).
Attanoos, et al., "Ileostomy polyps, adenomas, and adenocarcinomas," *Gut*, 37(6):840-844 (1995).
Baba, et al., "Construction of *Escherichia coli* K-12 in-frame, single-gene knockout mutants: the Keio collection," *Mol Syst Biol*, 2:2006-2008 (2006).
Bailey, "Complex Biology With No Parameters," *Nat Biotechnol*, 19(6):503-504 (2001).
Bailey, TL and Elkan, C, "Fitting a mixture model by expectation maximization to discover motifs in biopolymers," *Proc Int Conf Intell Syst Mol Biol*, 2:28-36 (1994).
Bailey, TL and Gribskov, M, "Combining evidence using p-values: application to sequence homology searches," *Bioinformatics*, 14(1):48-54 (1998).
Bairoch, A, and Apweiler, R, "The SWISS-PROT Protein Sequence database and its supplement TrEMBL in 2000," *Nucleic Acids Res*, 28(1):45-48 (2000).
Ball, et al., "Integrating functional genomic information into the *Saccharomyces* genome database," *Nucleic Acids Res*, 28(1):77-80 (2000).
Ban, et al., "Thymine and uracil catabolism in *Escherichia coli*," *J Gen Microbiol*, 73(2):267-272 (1972).
Bansal, "Integrating co-regulated gene-groups and pair-wise genome comparisons to automate reconstruction of microbial pathways," *Bioinformatics and Bioengineering Conference*, 209-216 (2001).
Bard, et al., "Sterol mutants of *Saccharomyces cerevisiae*: chromatographic analyses," *Lipids*, 12(8):645-654 (1977).
Baxevanis, "The Molecular Biology Database Collection: 2002 update," *Nucleic Acids Res*, 30:1-12 (2002).
Beard, et al., "Energy Balance for Analysis of Complex Metabolic Networks," *Biophys J*, 83(1):79-86 (2002).
Beckers, et al., "Large-Scale Mutational Analysis for the Annotation of the Mouse Genome," *Curr Opin Chem Biol*, 6(1)17-23 (2002).
Bell, et al., "Composition and functional analysis of the *Saccharomyces cerevisiae* trehalose synthase complex," *J Biol Chem.*, 273(50):33311-33319 (1998).
Benson, et al., "GenBank," *Nucleic Acids Res*, 28(1):15-18 (2000).
Berry, "Improving production of aromatic compounds in *Escherichia coli* by metabolic engineering," *Trends Biotechnol*, 14(7):250-256 (1996).
Bialy, "Living on the Edges," *Nat Biotechnol*, 19(2):111-112 (2001).
Bianchi, P, and Zanella, A, "Hematologically Important Mutations: Red Cell Pyruvate Kinase (Third Update)," *Blood Cells, Molecules, and Diseases*, 15:47-53 (2000).
Biaudet, et al., "Micado—a network-oriented database for microbial genomes," *Comput Appl Biosci*, 13(4):431-438 (1997).
Birkholz, "Fumarate reductase of *Helicobacter pylori*—an immunogenic protein," *J Med Microbiol*, 41(1):56-62 (1994).
Birner, et al., "Roles of phosphatidylethanolamine and of its several biosynthetic pathways in *Saccharomyces cerevisiae*," *Mol Biol Cell*, 12(4):997-1007 (2001).
Blackstock, WP and Weir, MP, "Proteomics: quantitative and physical mapping of cellular proteins," *Trends Biotechnol*, 17(3):121-127 (1999).
Bochner, "New technologies to assess genotype-phenotype relationships," *Nat Rev Genet*, 4(4):309-314 (2003).
Boles, E, et al., "Identification and characterization of MAE 1, the *Saccharomyces cerevisiae* structural gene encoding mitochondrial malic enzyme," *J Bacteriol.*, 180(11):2875-2882 (1998).
Boles, et al., "A family of hexosephosphate mutases in *Saccharomyces cerevisia*," *Eur J Biochem*, 220(1):83-96 (1994).
Boles, et al., "Characterization of a glucose-repressed pyruvate kinase (Pyk2p) in *Saccharomyces cerevisiae* that is catalytically insensitive to fructose-1,6-bisphosphate," *J Bacteriol*, 179(9):2987-2993 (1997).
Bonarius, et al., "Metabolic flux analysis of hybridoma cells in different culture media using mass balances," *Biotechnol Bioeng*, 50(3):299-318 (1996).
Bono, et al., "Reconstruction of amino acid biosynthesis pathways from the complete genome sequence," *Genome Research*, 8(3):203-210 (1998).
Bottomley, et al., "Cloning, sequencing, expression, purification and preliminary characterization of a type II dehydroquinase from *Helicobacter pylori*," *Biochem. J*, 319(Pt 2):559-565 (1996).
Bourot, S and Karst, F, "Isolation and characterization of the *Saccharomyces cerevisiae* SUT1 gene involved in sterol uptake," *Gene*, 165(1):97-102 (1995).
Burgard, AP and Maranas, CD, "Probing the Performance Limits of the *Escherichia coli* Metabolic Network Subject to Gene Additions or Deletions, *Biotechnol Bioeng*," 74(5):364-375 (2001).
Burgard, AP and Maranas, CD, "Review of the Enzymes and Metabolic Pathways (EMP) Database," *Metab Eng*, 3(3):193-194(2) (2001).
Burgard, et al., "Minimal reaction sets for *Escherichia coli* metabolism under different growth requirements and uptake environments," *Biotechnol Prog*, 17(5):791-797 (2001).
Burgard, et al., "Optknock: a bilevel programming framework for identifying gene knockout strategies for microbial strain optimization," *Biotechnol Bioeng*, 84(6):647-657 (2003).
Burns, "Acetyl-CoA carboxylase activity in *Helicobacter pylori* and the requirement of increased $CO_2$ for growth," *Microbiology*, 141(Pt 12):3113-3118 (1995).
Chalker, et al., "Systematic identification of selective essential genes in *Helicobacter pylori* by genome prioritization and allelic replacement mutagenesis," *J Bacteriol*, 183(4):1259-1268 (2001).
Chen, et al., "Characterization of the respiratory chain of *Helicobacter pylori*," *FEMS Immunol Med Microbiol*, 24(2):169-174 (1999).
Cherry, et al., "SGD: *Saccharomyces* Genome Database," *Nucleic Acids Res*, 26(1):73-79 (1998).
Ciriacy, M and Breitenbach, I, "Physiological effects of seven different blocks in glycolysis in *Saccharomyces cerevisiae*," *J Bacteriol*, 139(1):152-160 (1979).
Clarke, "Complete set of steady states for the general stoichiometric dynamical system," *J Chem Phys*, 75(10):4970-4979 (1981).
Clarke, "Stoichiometric network analysis," *Cell Biophys*, 12:237-253 (1988).
Clifton, D and Fraenkel, DG, "Mutant studies of yeast phosphofructokinase.," *Biochemistry*, 21(8):1935-1942 (1982).
Clifton, et al., "Glycolysis mutants in *Saccharomyces cerevisiae*.," *Genetics*, 88(1):1-11(1978).
Compan, I and Touati, D, et al., "Anaerobic activation of arcA transcription in *Escherichia coli*: roles of Fnr and ArcA," *Mol Microbiol*, 11(5):955-964 (1994).
Costanzo, et al., "YPD, PombePD and WormPD: model organism volumes of the BioKnowledge library, an integrated resource for protein information," *Nucleic Acids Res*, 29(1):75-9 (2001).
Cotter, et al., "Aerobic regulation of cytochrome d oxidase (cydAB) opoeron expression in *Escherichia coli*: roles of Fnr and ArcA in repression and activation," *Mol Microbiol*, 25(3):605-615 (1997).
Covert, et al., "Metabolic Modeling of Microbial Strains In Silico," *Trends Biochem Sci*, 26(3):179-186 (2001).
Covert, et al., "Regulation of Gene Expression in Flux Balance Models of Metabolism," *J Theor Biol*, 213(1):73-88 (2001).
Covert, MW and Palsson, BO, "Constraints-based models: Regulation of Gene Expression Reduces the Steady-state Solution Space," *J Theor Biol*, 216 (2003).
Covert, MW and Palsson, BO, "Transcriptional Regulation in Constraints-based Metabolic Models of *Escherichia coli*," *J Biol Chem*, 277(31):28058-28064 (2002).

(56) References Cited

OTHER PUBLICATIONS

Cupp, JR and McAlister-Henn, L, "Cloning and Characterization of the gene encoding the IDH1 subunit of NAD(+)-dependent isocitrate dehydrogenase from *Saccharomyces cerevisiae*," *J Biol Chem*, 267(23):16417-16423 (1992).
D'Haeseleer, et al., "Genetic network inference: from co-expression clustering to reverse engineering," *Bioinformatics*, 16(8):707-726 (2000).
Danchin, "Comparison Between the *Escherichia coli* and *Bacillus subtilis* Genomes Suggests That a Major Function of Polynucleotide Phosphorylase is to Synthesize CDP," DNA Research, 4(1):9-18 (1997).
Dandekar, et al., "Pathway Alignment: Application to the Comparative Analysis of Glycolytic Enzymes," *Biochem J*, 343(Pt 1):115-124 (1999).
Dantigny, et al., "A new control strategy for yeast production based on the L/A* approach," *Appl Microbiol Biotechnol*, 36:352-357 (1991).
Datsenko, KA and Wanner, BL, "One-step inactivation of chromosomal genes in *Escherichia coli* K-12 using PCR products," *Proc Natl Acad Sci U.S.A.*, 97(12):6640-6645 (2000).
Daum, et al., "Biochemistry, cell biology and molecular biology of lipids of *Saccharomyces cerevisiae*," *Yeast*, 14(16):1471-1510 (1998).
Daum, et al., "Systematic analysis of yeast strains with possible defects in lipid metabolism," *Yeast*, 15(7):601-614 (1999).
Dauner, et al., "*Bacillus subtilis* Metabolism and Energetics in Carbon-Limited and Excess-Carbon Chemostat Culture," *J Bacteriol*, 183(24):7308-7317 (2001).
Dauner, et al., "Metabolic Flux Analysis with a Comprehensive Isotopomer Model in *Bacillus subtilis*," *Biotechnol Bioeng*, 76(2):144-156 (2001).
Dauner, M and Sauer, U, "Stoichiometric Growth Model for Riboflavin-Producing *Bacillus subtilis*," *Biotechnol Bioeng*, 76(1):132-143 (2001).
de Jong, H., "Modeling and simulation of genetic regulatory systems: a literature review," *J Comput Biol*, 9(1):67-103 (2002).
De Reuse, et al., "The *Helicobacter pylori* ureC gene codes for a phosphoglucosamine mutase," *J Bacteriol*, 179(11):3488-3493 (1997).
Delgado and Liao, "Identifying Rate-Controlling Enzymes in Metabolic Pathways without Kinetic Parameters," *Biotechnol Prog*, 7:15-20 (1991).
Demain, et al., "Cellulase, clostridia, and ethanol," *Microbiol Mol Biol Rev*, 69(1):124-154 (2005).
Department of Energy, *Breaking the Biological Barriers to Cellulosic Ethanol* (2006).
DeRisi, et al.,"Exploring the Metabolic and Genetic Control of Gene Expression on a Genomic Scale," *Science*, 278(5338):680-686 (1997).
Devine, KM, "The *Bacillus subtilis* Genome Project: Aims and Progress," *Trends Biotechnol*, 13(6):210-216 (1995).
Dickson, "Sphingolipid Functions in *Sacchoromyces cerevisiae*: Comparison to Mammals," *Annu Rev Biochem*, 67:27-48 (1998).
Dickson, et al., "Serine palmitoyltransferase," *Methods Enzymol*, 311:3-9 (2000).
DiRusso, CC and Black, PN, "Long-chain fatty acid transport in bacteria and yeast. Paradigms for defining the mechanism underlying this protein-mediated process," *Mol Cell Biochem*, 192(1-2):41-52 (1999).
Edwards, et al., "Characterizing the Metabolic Phenotype: A Phenotype Phase Plane Analysis," *Biotech Bioeng*, 77(1):27-36 (2002).
Edwards, et al., "*In Silico* Predictions of *Escherichia coli* metabolic capabilities are Consistent with Experimental Data," *Nat Biotechnol*, 19(2):125-130 (2001).
Edwards, JS and Palsson, BO, "Robustness analysis of the *Escherichia coli* metabolic network," *Biotechnol Prog*, 16(6):927-939 (2000).

Edwards, JS, and Palsson, BO, "Metabolic flux analysis and the *in silico* analysis of *Escherichia colia* K-12 gene deletions," *BMC Bioinformatics*, 1:1-10 (2000).
Eisen, et al., "Cluster analysis and display of genome-wide expression patterns," *Proc Natl Acad Sci U.S.A.*, 95:14863-14868 (1998).
Eisenberg, et al., "Protein Function in the Post-Genomic Era," *Nature*, 405(6788):823-826 (2000).
Ermolaeva, et al., "Prediction of Operons in Microbial Genomes," *Nucl Acids Research*, 29(5):1216-1221 (2001).
Everitt, "Cluster Analysis 122," London:Heinemann (1974).
Fiehn, "Metabolomics—the link between genotypes and phenotypes," *Plant Mol Biol*, 48(1-2):155-171 (2002).
Finel, "Does NADH play a central role in energy metabolism in *Helicobacter pylori?*," *Trends Biochem Sci*, 23(11):412-413 (1998).
Fiorelli, et al., "Chronic non-spherocytic Haemolytic disorders associated with glucose-6-phosphate dehydrogenase variants," *Bailliere's Clinical Haematology*, 13:39-55 (2000).
Flikweert, et al., "Pyruvate decarboxylase: an indispensable enzyme for growth of *Saccharomyces cerevisiae* on glucose.," *Yeast*, 12(3):247-257 (1996).
Forst, "Network genomics—A Novel approach for the analysis of biological systems in the post-genomic era," *Molecular Biology Reports*, 29(3):265-280 (2002).
Forster, et al., "Large-scale evaluation of in silico gene deletions in *Saccharomyces cerevisiae*," *Omics*, 7(2)193-202 (2003).
Fraenkel, "The accumulation of glucose 6-phosphate from glucose and its effect in an *Escherichia coli* mutant lacking phosphoglucose isomerase and glucose 6-phosphate dehydrogenase," *J Biol Chem*, 243(24):6451-6457 (1968).
Fraser, et al., "Microbial genome sequencing," *Nature*, 406:799-803 (2000).
Fromont-Racine, et al., "Toward a functional analysis of the yeast genome through exhaustive two-hybrid screens," *Nat Genet*, 16(3):277-282 (1997).
Fukuchi, et al., "Isolation, overexpression and disruption of a *Saccharomyces cerevisiae* YNK gene encoding nucleoside diphosphate kinase," *Genes*, 129(1):141-146 (1993).
Gaasterland, T. and Selkov, E., "Reconstruction of Metabolic Networks Using Incomplete Information," *Proc Int Conf Intell Syst Mol Biol*, 3:127-135 (1995).
Gancedo, C and Delgado, MA, "Isolation and characterization of a mutant from *Saccharomyces cerevisiae* lacking fructose 1,6-bisphosphatase," *Eur J Biochem*, 139:651-655 (1984).
Gangloff, et al., "Molecular cloning of the yeast mitochondrial aconitase gene (ACO1) and evidence of a synergistic regulation of expression by glucose plus glutamate.," *Mol Cell Biol*, 10(7):3551-3561 (1990).
Glasner, et al., "ASAP, a systematic annotation package for community analysis of genomes," *Nucleic Acids Res*, 31(1):147-151 (2003).
Goffeau, A, "Four years of post-genomic life with 6000 yeast genes," *FEBS Lett*, 480(1):37-41 (2000).
Goryanin, et al., "Mathematical simulation and analysis of cellular metabolism and regulation," *Bioinformatics*, 15(9):749-758 (1999).
Goto, et al., "LIGAND database for enzymes, compounds and reactions," *Nucleic Acids Res*, 27(1):377-379 (1999).
Goto, et al., "LIGAND: chemical database for enzyme reactions," *Bioinformatics*, 14(7):591-599 (1998).
Grewal, et al., "Computer Modelling of the Interaction Between Human Choriogonadotropin and Its Receptor," *Protein Engineering*, 7(2):205-211 (1994).
Griffin, et al., "Complementary profiling of gene expression at the transcriptome and proteome levels in *Saccharomyces cerevisiae*," *Mol Cell Proteomics*, 1:323-333 (2002).
Grundy, et al., "Regulation of the *Bacillus subtilis* acetate kinase gene by CcpA." *J Bacteriol*, 175(22):7348-7355 (1993).
Guelzim, et al., "Topological and causal structure of the yeast transcriptional regulatory network," *Nat Genet*, 31(1):60-63 (2002).
Guetsova, et al., "The isolation and characterization of *Saccharomyces cerevisiae* mutants that constitutively express purine biosynthetic genes," *Genetics*, 147(2):383-397 (1997).

(56) References Cited

OTHER PUBLICATIONS

Hardison, et al., "Globin Gene Server: A Prototype E-Mail Database Server Featuring Extensive Multiple Alignments and Data Compilation for Electronic Genetic Analysis," *Genomics*, 21(2):344-353 (1994).
Hartig et al., "Differentially regulated malate synthase genes participate in carbon and nitrogen metabolism of *S. cerevisiae.*," *Nucleic Acids Res*, 20(21):5677-5686 (1992).
Hasty, et al., "Computational Studies of Gene Regulatory Networks: In Numero Molecular Biology," *Nat Rev Genet*, 2(4):268-279 (2001).
Hata, et al., "Characterization of a *Saccharomyces cerevisiae* mutant, N22, defective in ergosterol synthesis and preparation of [28-14C]ergosta-5,7-dien-3 beta-ol with the mutant," *J Biochem*, 94(2):501-510 (1983).
Hatzimanikatis, et al., "Analysis and Design of Metabolic Reaction Networks Via Mixed-Interger linear Optimization," *AIChE Journal*, 42(5):1277-1292 (1996).
Hazell, et al., "How *Helicobacter pylori* works: an overview of the metabolism of *Helicobacter pylori*," *Helicobacter*, 2(1):1-12 (1997).
Heijnen, et al., "Application of balancing methods in modeling the penicillin fermentation," *Biotechnology & Bioeng.*, 21:2175-2201 (1979).
Heinisch, et al., "Investigation of two yeast genes encoding putative isoenzymes of phosphoglycerate mutase.," *Yeast*, 14(3):203-213 (1998).
Heinrich, et al., "Metabolic regulation and mathematical models," *Prog Biophys Mol Biol*, 32(1):1-82 (1977).
Heinrich, et al., "Stoichiometric Analysis," *The Regulation of Cellular Systems*, xix:75-111 and 372, Chapman & Hall, New York (1996).
Henriksen, et al., "Growth energetics and metabolism fluxes in continuous cultures of *Penicillium chrysogenum*," *J of Biotechnol*, 45(2):149-164 (1996).
Heyer, et al., "Exploring expression data: identification and analysis of coexpressed genes," *Genome Res*, 9(11):1106-1115 (1999).
Holter, et al., "Dynamic modeling of gene expression data," *Proc Natl Acad Sci U.S.A.*, 98(4):1693-1698 (2001).
Holter, et al., "Fundamental patterns underlying gene expression profiles: simplicity from complexity," *Proc Natl Acad Sci U.S.A.*, 97:8409-9414 (2000).
Houghten, "Generation and use of synthetic peptide combinatorial libraries for basic research and drug discovery," *Nature*, 354(6348):84-86 (1991).
Hughes, et al., "Functional discovery via a compendium of expression profiles," *Cell*, 102(1):109-126 (2000).
Hughes, et al., "*Helicobacter pylori* porCDAB and oorDABC genes encode distinct pyruvate: flavodoxin and 2-oxoglutarate:acceptor oxidoreductases which mediate electron transport to NADP," *J Bacteriol*, 180(5):1119-1128 (1998).
Ideker, et al., "Integrated Genomic and Proteomic Analyses of a Systematically Perturbed Metabolic Network," *Science*, 292(5518):929-934 (2001).
Ince, JE and Knowles, CJ, "Ethylene formation by cell-free extracts of *Escherichia coli*," *Arch Microbiol*, 146(2):151-158 (1986).
Ishii, et al., "DBTBS: a database of *Bacillus subtilis* promoters and transcription factors," *Nucleic Acids Res*, 29(1):278-280 (2001).
Iyer, et al., "Genomic binding sites of the yeast cell-cycle transcription factors SBF and MBF," *Nature*, 409(6819):533-538 (2001).
Jamshidi, et al., "Dynamic simulation of the human red blood cell metabolic network," *Bioinformatics*, 17(3):286-287 (2001).
Jamshidi, et al., "In silico model-driven assessment of the effects of single nucleoptide polymorphins (SNPs) on human red blood cell-metabolism," *Genome Research*, 12(11):1687-1692 (2002).
Jenkins, LS and Nunn, WD, "Genetic and molecular characterization of the genes involved in short-chain fatty acid degradation in *Escherichia coli*: the ato system," *J Bacteriol*, 169(1):42-52 (1987).
Jenssen, et al., "A Literature Network of Human Genes for High-Throughput Analysis of Gene Expression," *Nat Genet*, 28(1):21-28 (2001).
Jorgensen, et al., "Metabolic flux distributions in *Penicillium chrysogenum* during fed-batch cultivations." *Biotechnol Bioeng*, 46(2):117-131 (1995).
Joshi, A and Palsson, BO, "Metabolic dynamics in the human red cell. Part I—A comprehensive kinetic model," *J Theor Biol*, 141(4):515-528 (1989).
Juty, et al., "Simultaneous Modeling of Metabolic, Genetic, and Product-Interaction Networks," *Briefings in Bioinformatics*, 2(3):223-232 (2001).
Kanehisa, M and Goto, S, "Kyoto Encyclopedia of Genes and Genomes database (KEGG)," *Nucleic Acids Res*, 28(1):27-30 (2000).
Karp, "An ontology for biological function based on molecular interactions," *Bioinformatics*, 16(3):269-285 (2000).
Karp, et al., "Eco Cyc: encyclopedia of *Escherichia coli* genes and metabolism," *Nucleic Acids Res*, 27(1):55-58 (1999).
Karp, et al., "HinCyc: A knowledge base of the complete genome and metabolic pathways of H. influenzae," *Proc Int Conf Intell Syst Mol Biol*, 4:116-124 (1996).
Karp, et al., "Integrated pathway-genome databases and their role in drug discovery.," *Trends Biotechnol*, 17(7):275-281 (1999).
Karp, et al., "The EcoCyc and MetaCyc databases," *Nucleic Acids Resarch*, 28(1):56-59 (2000).
Kather, et al., "Another unusual type of citric acid cycle enzyme in *Helicobacter pylori*: the malate:quinone oxidoreductase," *J Bacteriol*, 182(11):3204-3209 (2000).
Keating, et al., "An ethanologenic yeast exhibiting unusual metabolism in the fermentation of lignocellulosic hexose sugars," *J Ind Microbiol Biotechnol*, 31(5):235-244 (2004).
Kim, et al., "*Saccharomyces cerevisiae* contains two functional citrate synthase genes.," *Mol Cell Biol*, 6(6):1936-1942 (1986).
Kirkman, et al., "Red cell NADP+ and NADPH in glucose-6-phosphate dehydrogenase deficiency," *Journal of Clinical Investigation*, 55(4):875-878 (1975).
Kunst, et al., "The Complete Genome Sequence of the Gram-positive Bacterium *Bacillus subtilus*," *Nature*, 390(6557):249-256 (1997).
Lacroute, "Regulation of pyrimidine biosynthesis in *Saccharomyces cerevisiae*" *J Bacteriol*, 95(3):824-832 (1968).
Latif, F and Rajoka, MI, "Production of ethanol and xylitol from corn cobs by yeasts," *Bioresour Technol*, 77(1):57-63 (2001).
Lendenmann, U and Egli, T, "Is *Escherichia coli* growing in glucose-limited chemostat culture able to utilize other sugars without lag?," *Microbiology*, 141(Pt 1):71-78 (1995).
Leyva-Vasquez, MA and Setlow, P, "Cloning and nucleotide sequences of the genes encoding triose phosphate isomerase, phosphoglycerate mutase, and enolase from *Bacillus subtilis*," *J Bacteriol*, 176(13):3903-3910 (1994).
Li, C and Wong, WH, "Model-based analysis of oligonucleotide arrays: expression index computation and outlier detection," *Proc Natl Acad Sci U.S.A.*, 98(1):31-36 (2001).
Liao, et al., "Pathway Analysis, Engineering, and Physiological Considerations for Redirecting Central Metabolism," *Biotechnol Bioeng*, 52(1):129-140 (1996).
Liao, JC and Oh, MK, "Toward predicting metabolic fluxes in metabolically engineered strains," *Metab Eng*,1(3):214-223 (1999).
Link, et al., "Methods for generating precise deletions and insertions in the genome of wild-type *Escherichia coli*: Application to open reading frame characterization," *J Bacteriol*, 179(20):6228-6237 (1997).
Loftus, et al., "Isolation, characterization, and disruption of the yeast gene encoding cytosolic NADP-specific isocitrate dehydrogenase," *Biochemistry*, 33(32):9661-9667 (1994).
Lopez, et al., "The yeast inositol monophosphatase is a lithium- and sodium-sensitive enzyme encoded by a non-essential gene pair," *Mol Microbiol*, 31(4):1255-1264 (1999).
Marcelli, et al., "The respiratory chain of *Helicobacter pylori*: identification of cytochromes and the effects of oxygen on cytochrome and menaquinone levels," *FEMS Microbiol Lett*, 138(1):59-64 (1996).
McAdams, HH and Arkin, A, "Simulation of Prokaryotic Genetic Circuits," *Annual Review of Biophysics and Biomolecular Structure*, 27:199-224 (1998).

(56) References Cited

OTHER PUBLICATIONS

McAlister-Henn, L and Thompson, LM, "Isolation and expression of the gene encoding yeast mitochondrial malate dehydrogenase.," *J Bacteriol*, 169(11):5157-5166 (1987).
McGee, D.J., "*Helicobacter pylori* rocF is required for arginase activity and acid protection in vitro but is not essential for colonization of mice or for urease activity," *J Bacteriol*, 165(1):65-76 (1998).
Meldrum, "Automation for genomics, part one: preparation for sequencing," *Genome Res*, 10(8):1081-1092 (2000).
Mendes, P and Kell, D, "Non-linear optimization of biochemical pathways: Applications to metabolic engineering and parameter estimation," *Bioinformatics*, 14(10):869-883 (1998).
Mendz, et al., "Characterisation of glucose transport in *Helicobacter pylori*," *Biochim Biophys Acta*, 1244(2-3):269-276 (1995).
Mendz, et al., "Characterization of fumarate transport in *Helicobacter pylori*," *J Membr Biol*, 165(1):65-76 (1998).
Mendz, et al., "De novo synthesis of pyrimidine nucleotides by *Helicobacter pylon*," *J Appl Bacteriol*, 77(1):1-8 (1994).
Mendz, et al., "In situ characterization of *Helicobacter pylori* arginase," *Biochim Biophys Acta*, 1388(2):465-477 (1998).
Mendz, et al., "Purine metabolism and the microaerophily of *Helicobacter pylori*," *Arch Microbiol*, 168(6):448-456 (1997).
Mendz, et al., "The Entner-Doudoroff pathway in *Helicobacter pylori*," *Arch Biochem Biophys*, 312(2):349-356 (1994).
Mendz, GL and Hazell SL, "Aminoacid utilization by *Helicobacter pylori*," *Int J Biochem Cell Biol*, 27(10):1085-1093 (1995).
Mendz, GL and Hazell, SL, "Glucose phosphorylation in *Helicobacter pylori*," *Arch Biochem Biophys*, 300(1):522-525 (1993).
Mendz, GL, et al., "Pyruvate metabolism in *Helicobacter pylori*," *Arch Microbiol*, 162(3):187-192 (1994).
Mewes, et al., "MIPS: A database for genomes and protein sequences," *Nucleic Acids Research*, 30(1):31-34 (2002).
Mitchell, "The GLN1 locus of *Saccharomyces cerevisiae* encodes glutamine synthetase," *Genetics*, 111(2):243-258 (1985).
Moszer, "The Complete Genome of *Bacillus subtilis*: From Sequence Annotation to Data Management and Analysis," *FEBS Lett*, 430(1-2):28-36 (1998).
Moszer, et al., "SubtiList: the reference database for the *Bacillus subtilis* genome," *Nucleic Acids Res*, 30(1):62-65 (2002).
Mulquiney, PJ and Kuchel, PW, "Model of 2,3-bisphosphoglycerate metabolism in the human erythrocyte based on detailed enzyme kinetic equations: computer simulation and metabolic control analysis," *Biochem J*, 342(Pt 3):597-604 (1999).
Murray, M and Greenberg, ML, "Expression of yeast INM1 encoding inositol monophosphatase is regulated by inositol, carbon source and growth stage and is decreased by lithium and valproate," *Mol Microbiol*, 36(3):651-661 (2000).
Nedenskov, "Nutritional requirements for growth of *Helicobacter pylori*," *Appl Environ Microbiol*, 60(9):3450-3453 (1994).
Nissen, et al., "Expression of a cytoplasmic transhydrogenase in *Saccharomyces cerevisiae* results in formation of 2-oxoglutarate due to depletion of the NADPH pool," *Yeast*, 18(1):19-32 (2001).
Nissen, et al., "Flux distributions in anaerobic, glucose-limited continuous cultures of *Saccharomyces cerevisiae*," *Microbiology*, 143(Pt 1):203-218 (1997).
Ogasawara, "Systematic function analysis of *Bacillus subtilis* genes," *Res Microbiol*, 151(2):129-134 (2000).
Ogata, et al., "KEGG: Kyoto Encyclopedia of Genes and Genomes," *Nucleic Acids Res*, 27(1):29-34 (1999).
Oh, MK and Liao, JC, "Gene expression profiling by DNA microarrays and metabolic fluxes in *Escherichia coli*," *Biotech Prog*, 16:278-286 (2000).
Olsson, et al., "Separate and simultaneous enzymatic hydrolysis and fermentation of wheat hemicellulose with recombinant xylose utilizing *Saccharomyces cerevisiae*," *Appl Biochem Biotechnol*, 129-132:117-129 (2006).

Otto, et al., "A mathematical model for the influence of fructose 6-phosphate, ATP, potassium, ammonium and magnesium on the phosphofructokinase from rat erythrocytes," *Eur J Biochem*, 49(1):169-178 (1974).
Ouzounis, CA and Karp, PD, "Global Properties of the Metabolic Map of *Escherichia coli*," *Genome Res*, 10(4):568-576 (2000).
Overbeek, et al., "WIT: Integrated System for High-Throughput Genome Sequence Analysis and Metabolic Reconstruction" *Nucleic Acids Res*, 28(1):123-125 (2000).
Overkamp, et al., "In vivo analysis of the mechanisms for oxidation of cytosolic NADH by *Saccharomyces cerevisiae* mitochondria," *J Bacteriol*, 182(10):2823-2830 (2000).
Ozcan, S., Freidel, K., Leuker, A. & Ciriacy, M., "Glucose uptake and catabolite repression in dominant HTR1 mutants of *Saccharomyces cerevisiae.*," *J Bacteriol*, 175(17):5520-5528 (1993).
Pallotta, et al., "*Saccharomyces cerevisiae* mitochondria can synthesise FMN and FAD from externally added riboflavin and export them to the extramitochondrial phase," *FEBS Lett*, 428(3):245-249 (1998).
Palmieri, et al., "Identification and functions of new transporters in yeast mitochondria," *Biochim Biophys Acta*, 1459(2-3):363-369 (2000).
Palmieri, et al., "Identification of the yeast ACR1 gene product as a succinate-fumarate transporter essential for growth on ethanol or acetate," *FEBS Lett*, 417(1):114-118 (1997).
Palmieri, et al., "Identification of the yeast mitochondrial transporter for oxaloacetate and sulfate," *J Biol Chem*, 274(32):22184-22190 (1999).
Palmieri, et al., "Yeast mitochondrial carriers: bacterial expression, biochemical identification and metabolic significance," *J Bioenerg Biomembr*, 32(1):67-77 (2000).
Palsson, "The Challenges of in Silico (2000). Biology," *Nat Biotechnol*, 18(11):1147-1150 (2000).
Papin, et al., "The genome-scale metabolic extreme pathway structure in *Haemophilus influenzae* shows significant network redundancy," *J Theor Biol*, 215(1):67-82 (2002).
Parks, "Metabolism of sterols in yeast," *CRC Crit Rev Microbiol*, 6(4):301-341 (1978).
Parks, et al., "Use of sterol mutants as probes for sterol functions in the yeast, *Saccharomyces cerevisiae*," *Crit Rev Biochem Mol Biol*, 34(6):399-404 (1999).
Paulsen, et al., "Unified inventory of established and putative transporters encoded within the complete genome of *Saccharomyces cerevisiae*," *FEBS Lett*, 430(1-2):116-125 (1998).
Pearson, et al., "Comparison of DNA Sequences With Protein Sequences," *Genomics*, 46(1):24-36 (1997).
Persson, et al., "Phosphate permeases of *Saccharomyces cerevisiae*: structure, function and regulation," *Biochim Biophys Acta*, 1422(3):255-272 (1999).
Peterson, et al., "The Comprehensive Microbial Resource," *Nucleic Acids Res*, 29(1):123-125 (2001).
Pharkya, et al., "Exploring the overproduction of amino acids using the bilevel optimization framework OptKnock," *Biotechnol Bioeng*, 84(7):887-899 (2003).
Phelps, et al., "Metabolomics and microarrays for improved understanding of phenotypic characteristics controlled by both genomics and environmental constraints," *Curr Opin Biotechnol*, 13(1):20-24 (2002).
Pitson, et al., "The tricarboxylic acid cycle of *Helicobacter pylori*," *Eur J Biochem*, 260(1):258-267 (1999).
Price, et al., "Determination of redundancy and systems properties of the metabolic network of *Helicobacter pylori* using genome-scale extreme pathway analysis," *Genome Res*, 12(5):760-769 (2002).
Price, et al., "Genome-scale models of microbial cells: evaluating the consequences of constraints," *Nat Rev Microbiol*, 2(11):886-897 (2004).
Price, et al., "Network-based analysis of metabolic regulation in the human red blood cell," *J Theor Biol*, 225(2):185-194 (2003).
Przybyla-Zawislak, et al., "Genes of succinyl-CoA ligase from *Saccharomyces cerevisiae.*," *Eur J Biochem*, 258(2):736-743 (1998).
Qian, et al., "Ethanol production from dilute-Acid softwood hydrolysate by co-culture," *Appl Biochem Biotechnol*, 134(3):273-284 (2006).

(56) References Cited

OTHER PUBLICATIONS

Reed, et al., "An expanded genome-scale model of *Escherichia coli* K-12 (iJR904 GSM/GPR)," *Genome Biol*, 4(9):R54 (2003).
Reed, JL and Palsson, BO, "Thirteen years of building constraint-based in silico models of *Escherichia coli*" *J Bacteriol*, 185(9):2692-2699 (2003).
Regenberg, et al., "Substrate specificity and gene expression of the amino-acid permeases in *Saccharomyces cerevisiae*," *Curr Genet*, 36(6):317-328 (1999).
Remize, et al., "Engineering of the pyruvate dehydrogenase bypass in *Saccharomyces cerevisiae*: role of the cytosolic Mg(2+) and mitochondrial K(+) acetaldehyde dehydrogenases Ald6p and Ald4p in acetate formation during alcoholic fermentation," *Appl Environ Microbiol*, 66(8):3151-3159 (2000).
Ren, et al., "Genome-wide location and function of DNA binding proteins," *Science*, 290(5500):2306-2309 (2000).
Repetto, B and Tzagoloff, A, "In vivo assembly of yeast mitochondrial alpha-ketoglutarate dehydrogenase complex," *Mol Cell Biol*, 11(8):3931-3939 (1991).
Reynolds, DJ and Penn, CW, "Characteristics of *Helicobacter pylori* growth in a defined medium and determination of its amino acid requirements," *Microbiology*, 140(Pt. 10):2649-2656 (1994).
Rhee, et al., "Activation of gene expression by a ligand-induced conformational change of a protein-DNA complex," *J Biol Chem*, 273(18):11257-11266 (1998).
Romero, PR and Karp, P, "Nutrient-Related Analysis of Pathway/Genome Databases," *Pac Symp Biocomput*, 471-482 (2001).
Saier, MH, "Genome sequencing and informatics: new tools for biochemical discoveries," *Plant Physiol*, 117(4):1129-1133 (1998).
Salgado, et al., *Nucleic Acids Res*, 29(1):72-74 (2001).
Salmon, et al., "Global gene expression profiling in *Escherichia coli* K12. The effects of oxygen availability and FNR," *J Biol Chem*, 278(32):29837-29855 (2003).
Sauer, et al., "Metabolic flux ratio analysis of genetic and environmental modulations of *Escherichia coli* central carbon metabolism," *J Bacteriol*, 181(21):6679-6688 (1999).
Sauer, U and Bailey, JE, "Estimation of P-to-O Ratio in *Bacillus subtilis* and Its Influence on Maximum Riboflavin Yield," *Biotechnol Bioeng*, 64(6):750-754 (1999).
Sauer, Uwe, "Evolutionary Engineering of Industrially Important Microbial Phenotypes," *Adv in Biochem Eng Biotechnol*, 73:129-169 (2001).
Savageau, "Biochemical systems analysis. I. Some mathematical properties of the rate law for the component enzymatic reactions," *J Theor Biol*, 25(3):365-369 (1969).
Schaaff-Gerstenschlager, I and Zimmermann, FK, "Pentose-phosphate pathway in *Saccharomyces cerevisiae*: analysis of deletion mutants for transketolase, transaldolase, and glucose 6-phosphate dehydrogenase," *Curr Genet*, 24(5):373-376 (1993).
Schaff, et al., "the Virtual cell" *Proceedings of the Pacific Symposium on Biocomputing*, 4:228-239 (1999).
Schilling, CH and Palsson, BO, "Assessment of the Metabolic Capabilities of *Haemophilus influenzae* Rd Through a Genome-scale Pathway Analysis," *J Theor Biol*, 203(3):249-283 (2000).
Schilling, CH and Palsson, BO, "The Underlying Pathway Structure of Biochemical Reaction Networks," *Proc Natl Acad Sci U.S.A.*, 95(8):4193-4198 (1998).
Schilling, et al., "Combining Pathway Analysis with Flux Balance Analysis for the Comprehensive Study of Metabolic Systems," *Biotechnol Bioeng*, 71(4):286-306.
Schilling, et al., "Genome-scale metabolic model of *Helicobacter pylori* 26695," *J Bacteriol*, 184(16):4582-4593 (2002).
Schilling, et al., "Metabolic Pathway Analysis: Basic Concepts and Scientific Applications in the Post-genomic Era," *Biotechol Prog*, 15(3):296-303 (1999).
Schilling, et al., "Theory for the Systematic Definition of Metabolic Pathways and Their Use in Interpreting Metabolic Function from a Pathway-Oriented Perspective," *J Theor Biol*, 203(3):229-248 (2000).

Schneider, et al., "The *Escherichia coli* gabDTPC operon: specific gamma-aminobutyrate catabolism and nonspecific induction," *J Bacteriol*, 184(24):6976-6986.
Schuster, et al., "A general definition of metabolic pathways useful for systematic organization and analysis of complex metabolic networks," *Nature Biotechnol*, 18(3):326-332 (2000).
Schuster, et al., "Detection of elementary flux modes in biochemical networks: a promising tool for pathway analysis and metabolic engineering," *Trends Biotechnol*, 17(2):53-60 (1999).
Schuster, et al., "Exploring the pathway structure of metabolism: decomposition into subnetworks and application to *Mycoplasma pneumoniae*," *Bioinformatics*, 18(2):351-361 (2002).
Schuster, S and Hilgetag, C, "On elementary flux modes in biochemical reaction systems at steady state," *J Biol Syst*, 2(2):165-182 (1994).
Schwikowski, et al., "A network of protein-protein interactions in yeast," *Nature Biotechnol*, 18(12):1257-1261 (2000).
Selkov, et al., "A reconstruction of the metabolism of *Methanococcus jannaschii* from sequence data.," *Gene*, 197(1-2):GC11-26 (1997).
Selkov, et al., "Functional Analysis of Gapped Microbial Genomes: Amino Acid Metabolism of *Thiobacillus Ferroxidans*," *Proc Natl Acad Sci U.S.A.*, 97(7):3509-3514 (2000).
Selkov, et al., "MPW: the metabolic pathways database," *Nucleic Acids Res*, 26(1):43-45 (1998).
Shen-Orr, et al., "Network motifs in the transcriptional regulation network of *Escherichia coli*," *Nat Genet*, 31(1):64-68 (2002).
Skouloubris, et al., "The *Helicobacter pylori* UreI protein is not involved in urease activity but is essential for bacterial survival in vivo," *Infect Immun*, 66(9):4517-4521 (1998).
Smith, et al., "Functional analysis of the genes of yeast chromosome V by genetic footprinting.," *Science*, 274(5295):2069-2074 (1996).
Sorlie, et al., "Gene expression patterns of breast carcinomas distinguish tumor subclasses with clinical implications," *Proc Natl Acad Sci U.S.A.*, 98(19):10869-10874 (2001).
Stark, et al., "Amino acid utilisation and deamination of glutamine and asparagine by *Helicobacter pylori*," *J Med Microbiol*, 46(9):793-800 (1997).
Stephanopoulos, "Metabolic engineering," *Curr Opin Biotechnol*, 5(2):196-200 (1994).
Summers, et al., "*Saccharomyces cerevisiae* cho2 mutants are deficient in phospholipid methylation and cross-pathway regulation of inositol synthesis" *Genetics*, 120(4):909-922 (1988).
Swartz, "A PURE approach to constructive biology.," *Nat Biotechnol*, 19(8):732-733 (2001).
Syvanen, "Accessing genetic variation: Genotyping single nucleotide polymorphisms.," *Nat Rev Genet*, 2(12):930-942 (2001).
Szambelan, et al., "Use of *Zymomonas mobilis* and *Saccharomyces cerevisiae* mixed with *Kluyveromyces fragilis* for improved ethanol production from Jerusalem artichoke tubers," *Biotechnol Lett*, 26(10):845-848 (2004).
Tamayo, et al., "Interpreting patterns of gene expression with self-organizing maps: methods and application to hematopoietic differentation," *Proc Natl Acad Sci U.S.A.*, 96(6):2907-2912 (1999).
Tao, et al., "Engineering a homo-ethanol pathway in *Escherichia coli*: increased glycolytic flux and levels of expression of glycolytic genes during xylose fermentation," *J Bacteriol*, 183(10):2979-2988 (2001).
ter Linde, et al., "Genome-wide transcriptional analysis of aerobic and anaerobic chemostat cultures of *Saccharomyces cerevisiae*," *J Bacteriol*, 181(24):7409-7413 (1999).
Thomas, "Boolean Formalization of Genetic Control Circuits," *J Theor Biol*, 42(3):563-585 (1973).
Thomas, "Logical Analyses of Systems Comprising Feedback Loops," *J Theor Biol*, 73(4):631-656 (1978).
Thomas, D and Surdin-Kerjan, Y, "Metabolism of sulfur amino acids in *Saccharomyces cerevisiae*," *Microbiol Mol Biol Rev*, 61(4):503-532 (1997).
Tomb, et al., "The complete genome sequence of the gastric pathogen *Helicobacter pylori*," *Nature*, 388(6642):539-547 (1997).
Trotter, et al., "A genetic screen for aminophospholipid transport mutants identifies the phosphatidylinositol 4-kinase, STT4p, as an essential component in phosphatidylserine metabolism," *J Biol Chem*, 273(21):13189-13196 (1998).

(56) References Cited

OTHER PUBLICATIONS

Uetz, et al., "A comprehensive analysis of protein-protein interactions in *Saccharomyces cerevisiae*," *Nature*, 403(6770):623-627 (2000).
Van den Berg, MA and Steensma, HY, "ACS2, a *Saccharomyces cerevisiae* gene encoding acetyl-coenzyme A synthetase, essential for growth on glucose," *Eur J. Biochem*, 231(3):704-713 (1995).
van Dijken, et al., "Alcoholic fermentation by 'non-fermentative' yeasts," *Yeast*, 2(2):123-127 (1986).
van Dijken, et al., "Kinetics of growth and sugar consumption in yeasts," *Antonie Van Leeuwenhoek*, 63(3-4):343-352 (1993).
Vanrolleghem, et al., "Validation of a Metabolic Network for *Saccharomyces cerevisiae* Using Mixed Substrate Studies," *Biotechnol Prog*, 12(4):434-448 (1996).
Varma, A and Palsson, BO, "Metabolic capabilities of *Escherichia coli*. II: Optimal Growth Patterns.," *J Theor Biol*, 165:503-522 (1993).
Varma, A and Palsson, BO, "Metabolic capabilities of *Escherichia coli*: I. Synthesis of Biosynthetic Precursors and Cofactors," *J Theor Biol*, 165:477-502 (1993).
Varma, A and Palsson, BO, "Parametric senstivity of stoichiometric flux balance models applied to wild-type *Escherichia coli* metabolism," *Biotechnol Bioeng*, 45(1):69-79 (1995).
Varma, A and Palsson, BO, "Predictions for Oxygen Supply Control to Enhance Population Stability of Engineered Production Strains," *Biotechnol Bioeng*, 43(4):275-285 (1994).
Varma, A and Palsson, BO, "Stoichiometric flux balance models quantitatively predict growth and metabolic by-product secretion in wild-type *Escherichia coli* W3110," *Appl Environ Microbiol*, 60(10):3724-3731 (1994).
Varma, et al., "Biochemical Production Capabilities of *Escherichia coli*," *Biotechnol Bioeng*, 42(1):59-73 (1993).
Varma, et al., "Stoichiometric Interpretation of *Escherichia coli* Glucose Catabolism Under Various Oxygenation Rates.," *Appl Environ Microbiol*, 59(8):2465-2473 (1993).
Varner, J and Ramkrishna, D, "Mathematical Models of Metabolic Pathways," *Curr Opin Biotechnol*, 10(2):146-150 (1999).
Velculescu, et al., "Analysing uncharted transcriptomes with SAGE," *Trends Genet*, 16(10):423-425 (2000).
Verduyn, "Physiology of yeasts in relation to biomass yields," *Antonie Van Leeuwenhoek*, 60(3-4):325-353 (1991).
Verduyn, et al., "A theoretical evaluation of growth yields of yeasts," *Antonie Van Leeuwenhoek*, 59(1):49-63 (1991).
Verduyn, et al., "Energetics of *Saccharomyces cerevisiae* in anaerobic glucose-limited chemostat cultures," *J Gen Microbiol*, 136:405-412 (1990).
Vissing, et al., "Paradoxically Enhanced Glucose Production During Exercise in Humans with Blocked Glycolysis Caused by Muscle Phosphofructokinase Deficiency," *Neurology*, 47(3):766-771 (1996).
Wang, et al., "Computer-aided baker's yeast fermentations," *Biotechnol and Bioeng*, 19(1):69-86 (1977).
Wang, et al., "Computer Control of Bakers' Yeast Production," *Biotechnol and Bioeng*, 21:975-995 (1979).
Wen, et al., "Large-scale temporal gene expression mapping of central nervous system development," *Proc Natl Acad Sci U.S.A.*, 95(1):334-339 (1998).
Wiback, SJ and Palsson, BO, "Extreme pathway analysis of human red blood cell metabolism," *Biophys J*, 83:808-818 (2002).
Wieczorke, et al., "Concurrent knock-out of at least 20 transporter genes is required to block uptake of hexoses in *Saccharomyces cerevisiae*," *FEBS Lett*, 464(3):123-128 (1999).
Wingender, et al., "The TRANSFAC system on gene expression regulation," *Nucleic Acids Res*, 29(1):281-283 (2001).
Wong, P., et al., "Mathematical Model of the Lac Operon: Inducer Exclusion, Catabolite Repression, and Diauxic Growth on Glucose and Lactose," *Biotechnol Prog*, 13(2):132-143 (1997).
Yamada, et al., "Effects of common polymorphisms on the properties of recombinant human methylenetetrahydrofolate reductase," *Proc Natl Acad Sci U.S.A.*, 98(26):14853-14858 (2001).

Yeung, et al., "Reverse engineering gene networks using singular value decomposition and robust regression," *Proc Natl Acad Sci U.S.A.*, 99(9):6163-6168 (2002).
Yeung, et al., *Bioinformatics*, "Model-based clustering and data transformations for gene expression data," 17(10):977-87 (2001).
Yoshida, et al., "Combined transcriptome and proteome analysis as a powerful approach to study genes under glucose repression in *Bacillus subtilis*," *Nucleic Acids Res*, 29(3):683-692 (2001).
Zanella, A and Bianchi, P, "Red cell pyruvate kinase deficiency: from genetics to clinical manifestations," *Bailliere's Best Pract Res Clin Haematol* 13(1):57-81 (2000).
Zhu, J and Zhang, MO, "SCPD: a promoter database of the yeast *Saccharomyces cerevisiae*," *Bioinformatics*, 15(7-8):607-611 (1999).
Zweytick, et al., "Biochemical characterization and subcellular localization of the sterol C-24(28) reductase erg4p, from the yeast *Saccharomyces cerevisiae*," *FEBS Lett*, 470(1):83-87 (2000).
URL Dictionary.com pp. 1-2 (2004), Matrix.
URL Genome.jp Website, KEGG *Bacillus subtillis*, 1-7 (2005).
Akutsu, "Estimation Algorithm of Genetic Network," Mathmatical Science (Suri-Kagaku) 37(6)40-46 (1999). (Original and English translation submitted herewith), Mathematical Science.
Aristidou and Penttila, "Metabolic engineering applications to renewable resource utilization," *Curr. Opin. Biotechnol.* 11(2)187-198 (2000).
Benjamini and Hochberg, "Controlling the False Discovery Rate: A Practical and Powerful Approach to Multiple Testing," *J.R. Statist. Soc. B*. 57:289-300 (1995).
Callis, "Regulation of Protein Degradation," *Plant Cell* 7:845-857 (1995).
Chadha et al., "Hybrid process for ethanol production from rice straw," *Acta. Microbiol. Immunol. Hung*. 42(1):53-59 (1995).
Chadha et al., "Simultaneous saccharification and fermentation of rice straw into ethanol," *Acta. Microbiol. Immunol. Hung*. 42(1):71-75 (1995).
Christensen and Nielsen, "Metabolic network analysis. A powerful tool in metabolic engineering," *Adv. Biochem Engi Biotech*.66:209-231 (2000).
Clarke, "Stability of Complex Reaction Networks," *Adv. Chem. Physics* 43:1-125 (1980).
Cover and Blaser, "*Helicobacter pylori* infection, a paradigm for chronic mucosal inflammation: pathogenesis and implications for eradication and prevention," *Adv. Intern. Med*. 41:85-117 (1996).
Dafoe et al., "In Silico Knowledge Discovery Biomedical databases," Proceedings of the SPIE Fifth Workshop on Neural Networks, San Francisco, Nov. 7-10, 1993.
Dooley et al., "An all D-amino acid opiod peptide with central analgesic activity from a combinatorial library," *Science* 266(5193):2019-2022 (1994).
Duarte et al., "Reconstruction and validation of *Saccharomyces cerevisiae* iND750, a fully compartmentalized genome-scale metabolic model," *Genome Res*. 14(7):1298-1309 (2004).
Edwards and Palsson, "The *Escherichia coli* MG1655 in silico Metabolic Genotype: Its Definition, Characteristics, and Capabilities," *Proc. Natl. Acad. Sci. USA* 97(10):5528-5533 (2000).
Edwards et al., "Characterizing Phenotypic Plasticity: A Phase Plane Analysis," *BMES/EMBS Conference, Proceedings of the First Joint* vol. 2, p. 1217 (1999).
Feist and Palsson, "The growing scope of applications of genome-scale metabolic reconstructions using *Escherichia coli*," *Nat. Biotech*. 26(6):659-667 (2008).
Fleischmann, "Whole-genome random sequencing and assembly of *Haemophilus influenzae* Rd," *Science* 269(5223):496-512 (1995).
Ge, et al., "Cloning and functional characterization of *Helicobacter pylori* fumarate reductase operon comprising three structural genes coding for subunits C, A and B," *Gene* 204(1-2):227-234 (1997).
Kelly, "The physiology and metabolism of the human gastric pathogen *Helicobacter pylori*," *Adv. Microb. Physiol*. 40:137-189 (1998).
Kremling, et al., "The organization of metabolic reaction networks. III. Application for diauxic growth on glucose and lactose," *Metab. Eng*. 3(4):362-379 (2001).

(56) References Cited

OTHER PUBLICATIONS

Mahadevan and Schilling, "The effects of alternate optimal solutions in constraint-based genome-scale metabolic models," *Metab. Eng.* 5(4):264-276 (2003).
Marshall and Warren, "Unidentified curved bacilli in the stomach of patients with gastritis and peptic ulceration," *Lancet* 1(8390):1311-1315 (1984).
McAdams and Shapiro, "Circuit simulation of genetic networks." *Science* 269(5224):650-656 (1995).
Mendz et al., "Fumarate reductase: a target for therapeutic intervention against *Helicobacter pylori*," *Arch. Biochem. Biophys.* 321(1):153-159 (1995).
Mendz et al., "Glucose utilization and lactate production by *Helicobacter pylori*," *J. Gen. Microbiol.* 139(12):3023-3028 (1993).
Mendz and Hazell, "Fumarate catabolism in *Helicobacter pylori*," *Biochem. Mol. Biol. Int.* 31(2):325-332 (1993).
Mendz et al., "Salvage synthesis of purine nucleotides by *Helicobacter pylori*," *J. Appl. Bacteriol.* 77(6):674-681 (1994).
Palsson, "What Lies Beyond Bioinformatics," *Nat. Biotech.* 15:3-4 (1997).
Patel and West, "Degradation of the pyrimidine bases uracil and thymine by *Escherichia coli B" Microbios*. 49(199):107-113 (1987).
Raclot et al., "Selective release of human adipocyte fatty acids according to molecular structure," *Biochem. J.* 324 (Pt3):911-915 (1997).
Sauer et al., "Metabolic Capacity of *Bacillus subtilis* for the Production of Purine Nucleosides, Riboflavin, and Folic Acid," *Biotechnol. Bioeng*, 59(2):227-238 (1998).
Savinell and Palsson, "Network Analysis of Intermediary Metabolism using Linear Optimization. II. Interpretation of Hybridoma Cell Metabolism," *J. Theor. Biol.* 154:455-473 (1992).
Savinell and Palsson, "Network Analysis of Intermediary Metabolism using Linear Optimization. I. Development of Mathematical Formalism," *J Theor Biol* 154:421-454 (1992).
Schena, et al., "Quantitative monitoring of gene expression patterns with a complementary DNA microarray," *Science* 270(5235):467-470 (1995).
Schilling and Palsson, "The Underlying Pathway Structure of Biochemical Reaction Networks," *Proc. Natl. Acad. Sci. USA* 95(8):4193-4198 (1998).
Schilling, "On Systems Biology and the Pathway Analysis of Metabolic Networks," Department of Bioengineering, University of California, San Diego: La Jolla 198-241 (2000).
Sedivy and Fraenkel, "Fructose bisphosphatase of *Saccharomyces cerevisiae*. Cloning, dusruption and regulation of the FBP1 sructural gene.," *J. Mol. Biol.* 186(2):307-319 (1985).
Selkov, et al., "The metabolic pathway collection from EMP: the enzymes and metabolic pathways database," *Nucleic Acids Res.* 24(1):26-28 (1996).
Sherlock, et al., "The physiology of L-methionine catabolism to the secondary metabolite ethylene by *Escherichia coli*," *Curr. Opin. Immunol.* 12:201-205 (2000).
Shipston and Bunch, "The physiology of L-methionine catabolism to the secondary metabolite ethylene by *Escherichia coli*," *J. Gen. Microbiol.* 135(6), 1489-1497 (1989).
Silve, et al., The immunosuppressant SR 31747 blocks cell proliferation by inhibiting a steroid isomerase in *Saccharomyces cerevisiae, Mol. Cell Biol.* 16(6):2719-2727 (1996).
Tanaka and Zerez, "Red cell enzymopathies of the glycolytic pathway," *Semin. Hematol.* 27(2):165-185 (1990).
Tandeitnik, et al., "Modeling of biological neurons by artificial neural networks," Nineteenth Convention of Electrical and Electronics Engineers in Israel, Jerusalem, Israel, New York, NY USA, pp. 239-242 (1996).
Taniguchi and Tanaka, "Clarification of interactions among microorganisms and development of co-culture system for production of useful substances," *Adv. Biochem. Eng. Biotechnol.* 90:35-62 (2004).

Venter, et al., "Shotgun sequencing of the human genome," *Science* 280(5639):1540-1542 (1998).
Vo, et al., "Reconstruction and functional characterization of the human mitochondrial metabolic network abased on proteomic and biochemical data," *J. Biol. Chem.* 279(38):39532-39540 (2004).
Waterston and Sulston, "The Human Genome Project: reaching the finish line," *Science* 282(5386):53-54 (1998).
Wills and Melham, "Pyruvate carboxylase deficiency in yeast: a mutant affecting the interaction between the glyoxylate and Krebs cycles.," *Arch. Biochem. Biophys.* 236(2):782-791 (1985).
Winzeler, et al., "Functional characterization of the *S. cerevisiae* genome by gene deletion and parallel analysis," *Science* 285(5429):901-906 (1999).
Xie and Wang, "Material Balance Studies on Animal Cell Metabolism Using a Stoichiometrically Based Reaction Network," *Biotech. Bioeng.* 52:579-590 (1996).
Xie and Wang, "Energy Metabolism and ATP Balance in Animal Cell Cultivation Using a Stoichiometrically Based Reaction Network," *Biotech. Bioeng.* 52:591-601 (1996).
Zeng, et al., "Use of respiratory quotient as a control parameter for optimum oxygen supply and scale-up of 2,3-butanediol production under microaerobic conditions," *Biotechnol. Bioeng.* 44(9):1107-1114 (1994).
Zigova, "Effect of RQ and pre-seed conditions on biomass and galactosyl transferase production during fed-batch culture of *S. cerevisiae* BT150," *J. Biotechnol.* 80(1):55-62 (2000).
URL affymetrix.com/index.affx; Date Obtained: Sep. 18, 2009, Home page 1 page.
URL affymetrix.com/products/arrays/specific/ecoli antisense.affx.: Date Obtained: Sep. 18, 2009, Home page, 1 page.
URL asap.ahabs.wisc.edu/annotation/php/logon.php, The ASAP website.; Date Obtained: Sep. 7, 2009, Home page, 1 page.
URL ca.expasy.org/sprot/, protein database SWISS—PROT: Date Obtained: Jun. 15, 2009, Home page, 2 pages.
URL dchip.org, dChip software; Date Obtained Jun. 15, 2009.
URL Dictionary.com pp. 1-2 (2004), Matrix; Date Obtained Nov. 1, 2004.
URL enzobio.com/lifesci__index.htm, Enzo BioArray Terminal Labeling Kit protocol; Date Obtained Sep. 18, 2009.
URL genetics.wisc.edu/, *E. coli* Genome Project at the University of Wisconsin; Date Obtained Sep. 18, 2009, Home page, 1 page total.
URL Genome.jp Website, KEGG *Bacillus subtillis*, 1-7; Date Obtained Jun. 1, 2005, Home page.
URL genome.tugraz.at/Software/Genesis/Description.html, "Genesis" software; Date Obtained: Sep. 18, 2009, Home page, 1 page total.
URL integratedgenomics.com, ERGO from Integrated Genomics; Date Obtained Sep. 18, 2009.
URL ncbi.nlm.nih.gov/entrez/query.fcgi?db=Genome, The NCBI Entrez Genome database; Date Obtained Jun. 15, 2009, Home page, 1 page.
URL ncbi.nlm.nih.gov/LocusLink/, LocusLink database maintained by the NCBI; Date Obtained Jun. 15, 2009, Home page, 1 page.
URL ncbi.nlm.nih.gov/Taxonomy/taxonomyhome.html/; Date Obtained Sep. 18, 2009, 1 page.
URL nslij-genetics.org/search_omim.html, Online Mendelian Inheritance in Man database, Center for Medical Genetics, Johns Hopkins University (Baltimore, MD) and National Center for Biotechnology Information, National Library of Medicine (Bethesda, MD); Date Obtained Sep. 18, 2009, Home page, 2 pages.
URL qiagen.com, Qiagen RNeasy Mini Kit; Date Obtained Sep. 18, 2009, Home page, 1 page.
URL rana.lbl.gov/EisenSoftware.htm, "Cluster" software; Date Obtained Sep. 18, 2009, 3 pages.
URL. www.i-sis.org.uk/WITBRL.php; Hoppert, M; Date Obtained Nov. 23, 2008.

\* cited by examiner

Figure 3

METHODS FOR IDENTIFYING DRUG TARGETS BASED ON GENOMIC SEQUENCE DATA

RELATED APPLICATIONS

This application in a continuation of application Ser. No. 09/243,022, filed Feb. 2, 1999 now abandoned.

BACKGROUND OF THE INVENTION

1. Field of the Invention

This invention relates to methods for identifying drug targets based on genomic sequence data. More specifically, this invention relates to systems and methods for determining suitable molecular targets for the directed development of antimicrobial agents.

2. Description of the Related Art

Infectious disease is on a rapid rise and threatens to regain its status as a major health problem. Prior to the discovery of antibiotics in the 1930s, infectious disease was a major cause of death. Further discoveries, development, and mass production of antibiotics throughout the 1940s and 1950s dramatically reduced deaths from microbial infections to a level where they effectively no longer represented a major threat in developed countries.

Over the years antibiotics have been liberally prescribed and the strong selection pressure that this represents has led to the emergence of antibiotic resistant strains of many serious human pathogens. In some cases selected antibiotics, such as vancomycin, literally represent the last line of defense against certain pathogenic bacteria such as *Staphylococcus*. The possibility for staphylococci to acquire vancomycin resistance through exchange of genetic material with enterococci, which are commonly resistant to vancomycin, is a serious issue of concern to health care specialists. The pharmaceutical industry continues its search for new antimicrobial compounds, which is a lengthy and tedious, but very important process. The rate of development and introduction of new antibiotics appears to no longer be able to keep up with the evolution of new antibiotic resistant organisms. The rapid emergence of antibiotic resistant organisms threatens to lead to a serious widespread health care concern.

The basis of antimicrobial chemotherapy is to selectively kill the microbe with minimal, and ideally no, harm to normal human cells and tissues. Therefore, ideal targets for antibacterial action are biochemical processes that are unique to bacteria, or those that are sufficiently different from the corresponding mammalian processes to allow acceptable discrimination between the two. For effective antibiotic action it is clear that a vital target must exist in the bacterial cell and that the antibiotic be delivered to the target in an active form. Therefore resistance to an antibiotic can arise from: (i) chemical destruction or inactivation of the antibiotic; (ii) alteration of the target site to reduce or eliminate effective antibiotic binding; (iii) blocking antibiotic entry into the cell, or rapid removal from the cell after entry; and (iv) replacing the metabolic step inhibited by the antibiotic.

Thus, it is time to fundamentally re-examine the philosophy of microbial killing strategies and develop new paradigms. One such paradigm is a holistic view of cellular metabolism. The identification of "sensitive" metabolic steps in attaining the necessary metabolic flux distributions to support growth and survival that can be attacked to weaken or destroy a microbe, need not be localized to a single biochemical reaction or cellular process. Rather, different cellular targets that need not be intimately related in the metabolic topology could be chosen based on the concerted effect the loss of each of these functions would have on metabolism.

A similar strategy with viral infections has recently proved successful. It has been shown that "cocktails" of different drugs that target different biochemical processes provide enhanced success in fighting against HIV infection. Such a paradigm shift is possible only if the necessary biological information as well as appropriate methods of rational analysis are available. Recent advances in the field of genomics and bioinformatics, in addition to mathematical modeling, offer the possibility to realize this approach.

At present, the field of microbial genetics is entering a new era where the genomes of several microorganisms are being completely sequenced. It is expected that in a decade, or so, the nucleotide sequences of the genomes of all the major human pathogens will be completely determined. The sequencing of the genomes of pathogens such as *Haemophilus influenzae* has allowed researchers to compare the homology of proteins encoded by the open reading frames (ORFs) with those of *Escherichia coli*, resulting in valuable insight into the *H. influenzae* metabolic features. Similar analyses, such as those performed with *H. influenzae*, will provide details of metabolism spanning the hierarchy of metabolic regulation from bacterial genomes to phenotypes.

These developments provide exciting new opportunities to carry out conceptual experiments in silico to analyze different aspects of microbial metabolism and its regulation. Further, the synthesis of whole-cell models is made possible. Such models can account for each and every single metabolic reaction and thus enable the analysis of their role in overall cell function. To implement such analysis, however, a mathematical modeling and simulation framework is needed which can incorporate the extensive metabolic detail but still retain computational tractability. Fortunately, rigorous and tractable mathematical methods have been developed for the required systems analysis of metabolism.

A mathematical approach that is well suited to account for genomic detail and avoid reliance on kinetic complexity has been developed based on well-known stoichiometry of metabolic reactions. This approach is based on metabolic flux balancing in a metabolic steady state. The history of flux balance models for metabolic analyses is relatively short. It has been applied to metabolic networks, and the study of adipocyte metabolism. Acetate secretion from *E. coli* under ATP maximization conditions and ethanol secretion by yeast have also been investigated using this approach.

The complete sequencing of a bacterial genome and ORF assignment provides the information needed to determine the relevant metabolic reactions that constitute metabolism in a particular organism. Thus a flux-balance model can be formulated and several metabolic analyses can be performed to extract metabolic characteristics for a particular organism. The flux balance approach can be easily applied to systematically simulate the effect of single, as well as multiple, gene deletions. This analysis will provide a list of sensitive enzymes that could be potential antimicrobial targets.

The need to consider a new paradigm for dealing with the emerging problem of antibiotic resistant pathogens is a problem of vital importance. The route towards the design of new antimicrobial agents must proceed along directions that are different from those of the past. The rapid growth in bioinformatics has provided a wealth of biochemical and genetic information that can be used to synthesize complete representations of cellular metabolism. These models can be analyzed with relative computational ease through flux-balance models and visual computing techniques. The ability to analyze the global metabolic network and understand the robustness and sensitivity of its regulation under various growth conditions offers promise in developing novel methods of antimicrobial chemotherapy.

In one example, Pramanik et al. described a stoichiometric model of *E. coli* metabolism using flux-balance modeling techniques (Stoichiometric Model of *Escherichia coli* Metabolism: Incorporation of Growth-Rate Dependent Biomass Composition and Mechanistic Energy Requirements, *Biotechnology and Bioengineering*, Vol. 56, No. 4, Nov. 20, 1997). However, the analytical methods described by Pramanik, et al. can only be used for situations in which biochemical knowledge exists for the reactions occurring within an organism. Pramanik, et al. produced a metabolic model of metabolism for *E. coli* based on biochemical information rather than genomic data since the metabolic genes and related reactions for *E. coli* had already been well studied and characterized. Thus, this method is inapplicable to determining a metabolic model for organisms for which little or no biochemical information on metabolic enzymes and genes is known. It can be envisioned that in the future the only information we may have regarding an emerging pathogen is its genomic sequence. What is needed in the art is a system and method for determining and analyzing the entire metabolic network of organisms whose metabolic reactions have not yet been determined from biochemical assays. The present invention provides such a system.

SUMMARY OF THE INVENTION

This invention relates to constructing metabolic genotypes and genome specific stoichiometric matrices from genome annotation data. The functions of the metabolic genes in the target organism are determined by homology searches against databases of genes from similar organisms. Once a potential function is assigned to each metabolic gene of the target organism, the resulting data is analyzed. In one embodiment, each gene is subjected to a flux-balance analysis to assess the effects of genetic deletions on the ability of the target organism to produce essential biomolecules necessary for its growth. Thus, the invention provides a high-throughput computational method to screen for genetic deletions which adversely affect the growth capabilities of fully sequenced organisms.

Embodiments of this invention also provide a computational, as opposed to an experimental, method for the rapid screening of genes and their gene products as potential drug targets to inhibit an organism's growth. This invention utilizes the genome sequence, the annotation data, and the biomass requirements of an organism to construct genomically complete metabolic genotypes and genome-specific stoichiometric matrices. These stoichiometric matrices are analyzed using a flux-balance analysis. This invention describes how to assess the affects of genetic deletions on the fitness and productive capabilities of an organism under given environmental and genetic conditions.

Construction of a genome-specific stoichiometric matrix from genomic annotation data is illustrated along with applying flux-balance analysis to study the properties of the stoichiometric matrix, and hence the metabolic genotype of the organism. By limiting the constraints on various fluxes and altering the environmental inputs to the metabolic network, genetic deletions may be analyzed for their affects on growth. This invention is embodied in a software application that can be used to create the stoichiometric matrix for a fully sequenced and annotated genome. Additionally, the software application can be used to further analyze and manipulate the network so as to predict the ability of an organism to produce biomolecules necessary for growth, thus, essentially simulating a genetic deletion.

DETAILED DESCRIPTION OF THE INVENTION

This invention relates to systems and methods for utilizing genome annotation data to construct a stoichiometric matrix representing most of all of the metabolic reactions that occur within an organism. Using these systems and methods, the properties of this matrix can be studied under conditions simulating genetic deletions in order to predict the affect of a particular gene on the fitness of the organism. Moreover, genes that are vital to the growth of an organism can be found by selectively removing various genes from the stoichiometric matrix and thereafter analyzing whether an organism with this genetic makeup could survive. Analysis of these lethal genetic mutations is useful for identifying potential genetic targets for anti-microbial drugs.

It should be noted that the systems and methods described herein can be implemented on any conventional host computer system, such as those based on Intel® microprocessors and running Microsoft Windows operating systems. Other systems, such as those using the UNIX or LINUX operating system and based on IBM®, DEC® or Motorola® microprocessors are also contemplated. The systems and methods described herein can also be implemented to run on client-server systems and wide-area networks, such as the Internet.

Software to implement the system can be written in any well-known computer language, such as Java, C, C++, Visual Basic, FORTRAN or COBOL and compiled using any well-known compatible compiler.

The software of the invention normally runs from instructions stored in a memory on the host computer system. Such a memory can be a hard disk, Random Access Memory, Read Only Memory and Flash Memory. Other types of memories are also contemplated to function within the scope of the invention.

Figure 1:
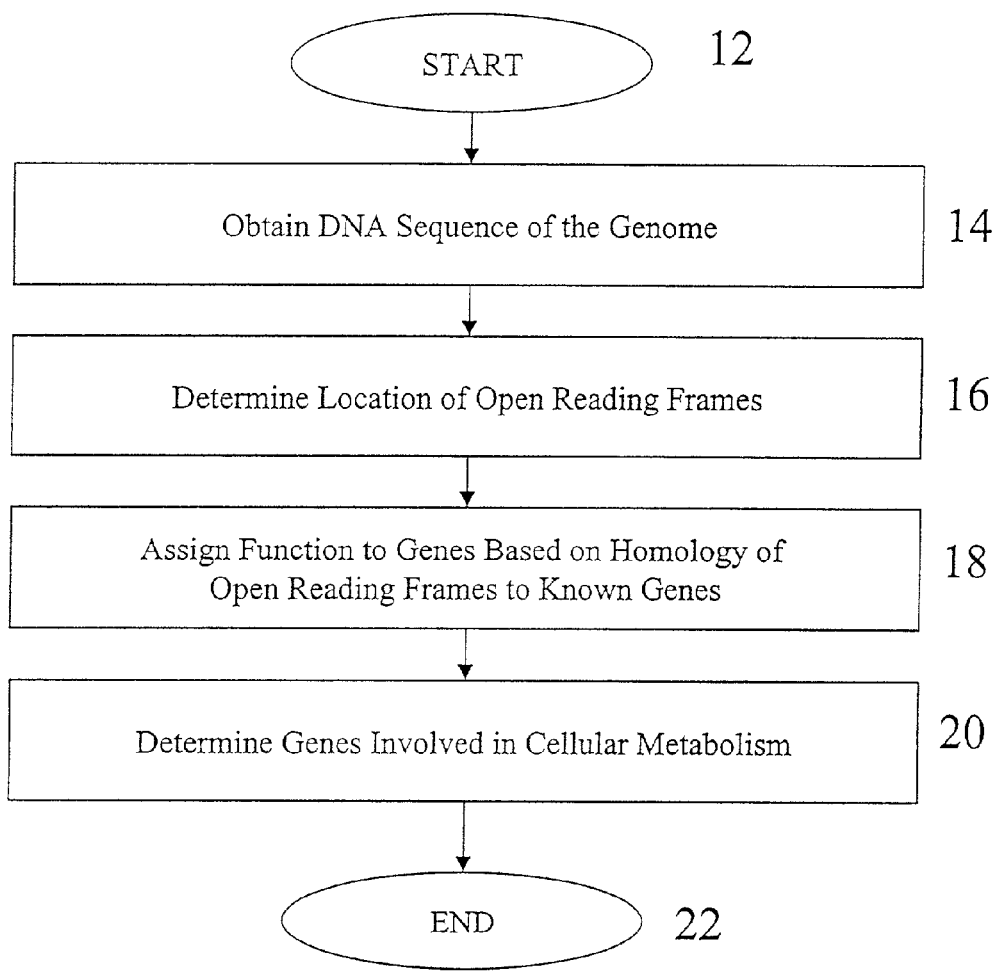
FIG. 1 is a flow diagram illustrating one procedure for creating metabolic genotypes from genomic sequence data for any organism.

A process 10 for producing metabolic genotypes from an organism is shown in FIG. 1. Beginning at a start state 12, the process 10 then moves to a state 14 to obtain the genomic DNA sequence of an organism. The nucleotide sequence of the genomic DNA can be rapidly determined for an organism with a genome size on the order of a few million base pairs. One method for obtaining the nucleotide sequences in a genome is through commercial gene databases. Many gene sequences are available on-line through a number of sites and can easily be downloaded from the Internet. Currently, there are 16 microbial genomes that have been fully sequenced and are publicly available, with countless others held in proprietary databases. It is expected that a number of other organisms, including pathogenic organisms will be found in nature for which little experimental information, except for its genome sequence, will be available.

Once the nucleotide sequence of the entire genomic DNA in the target organism has been obtained at state 14, the coding regions, also known as open reading frames, are determined at a state 16. Using existing computer algorithms, the location of open reading frames that encode genes from within the genome can be determined. For example, to identify the proper location, strand, and reading frame of an open reading frame one can perform a gene search by signal (promoters, ribosomal binding sites, etc.) or by content (positional base frequencies, codon preference). Computer programs for determining open reading frames are available, for example, by the University of Wisconsin Genetics Computer Group and the National Center for Biotechnology Information.

After the location of the open reading frames have been determined at state 16, the process 10 moves to state 18 to assign a function to the protein encoded by the open reading frame. The discovery that an open reading frame or gene has sequence homology to a gene coding for a protein of known function, or family of proteins of known function, can provide the first clues about the gene and it's related protein's function. After the locations of the open reading frames have been determined in the genomic DNA from the target organism, well-established algorithms (i.e. the Basic Local Alignment Search Tool (BLAST) and the FAST family of programs can be used to determine the extent of similarity between a given sequence and gene/protein sequences deposited in worldwide genetic databases. If a coding region from a gene in the target organism is homologous to a gene within one of the sequence databases, the open reading frame is assigned a function similar to the homologously matched gene. Thus, the functions of nearly the entire gene complement or genotype of an organism can be determined so long as homologous genes have already been discovered.

All of the genes involved in metabolic reactions and functions in a cell comprise only a subset of the genotype. This subset of genes is referred to as the metabolic genotype of a particular organism. Thus, the metabolic genotype of an organism includes most or all of the genes involved in the organism's metabolism. The gene products produced from the set of metabolic genes in the metabolic genotype carry out all or most of the enzymatic reactions and transport reactions known to occur within the target organism as determined from the genomic sequence.

To begin the selection of this subset of genes, one can simply search through the list of functional gene assignments from state 18 to find genes involved in cellular metabolism. This would include genes involved in central metabolism, amino acid metabolism, nucleotide metabolism, fatty acid and lipid metabolism, carbohydrate assimilation, vitamin and cofactor biosynthesis, energy and redox generation, etc. This subset is generated at a state 20. The process 10 of determining metabolic genotype of the target organism from genomic data then terminates at an end stage 22.

Figure 2:
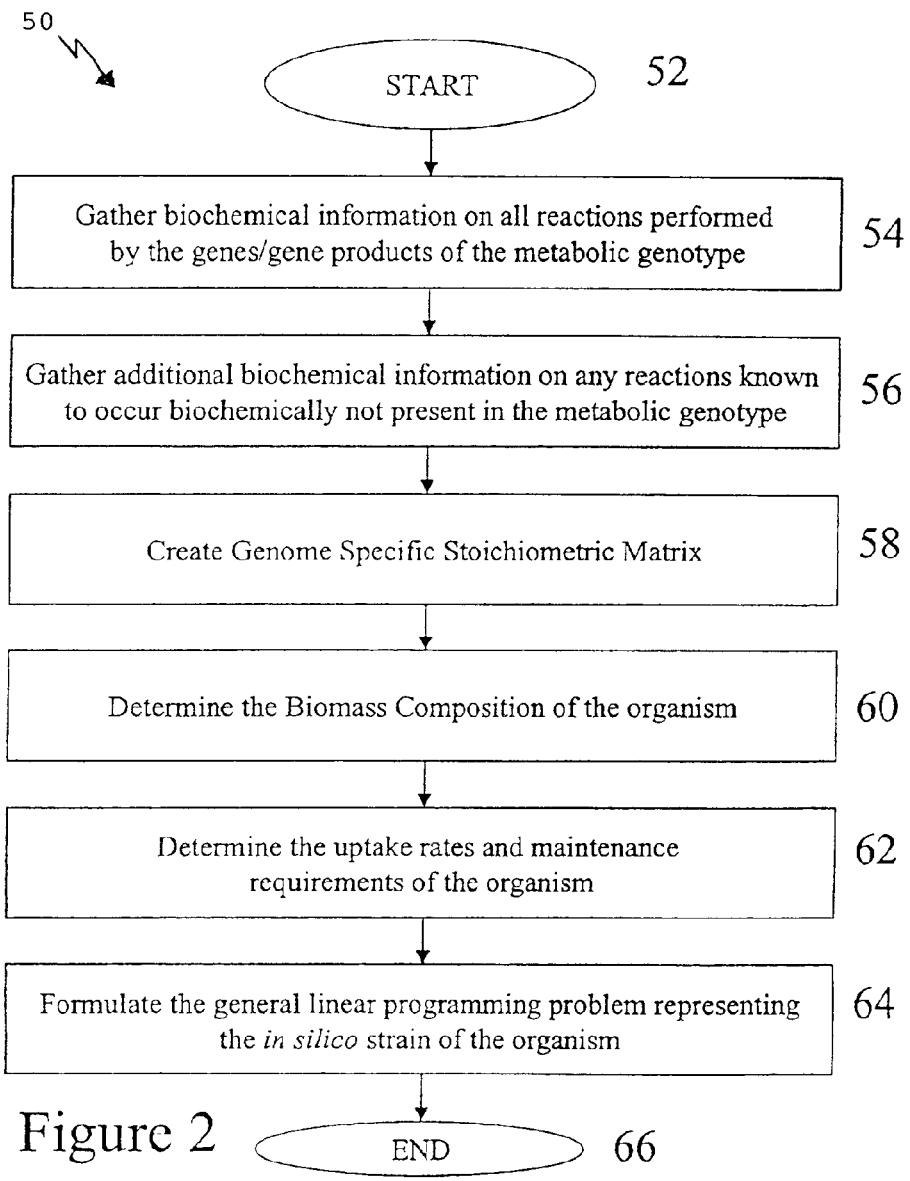
FIG. 2 is a flow diagram illustrating one procedure for producing in silico microbial strains from the metabolic genotypes created by the method of FIG. 1, along with additional biochemical and microbiological data.

Referring now to FIG. 2, the process 50 of producing a computer model of an organism. This process is also known as producing in silico microbial strains. The process 50 begins at a start state 52 (same as end state 22 of process 10) and then moves to a state 54 wherein biochemical information is gathered for the reactions performed by each metabolic gene product for each of the genes in the metabolic genotype determined from process 10.

For each gene in the metabolic genotype, the substrates and products, as well as the stoichiometry of any and all reactions performed by the gene product of each gene can be determined by reference to the biochemical literature. This includes information regarding the irreversible or reversible nature of the reactions. The stoichiometry of each reaction provides the molecular ratios in which reactants are converted into products.

Potentially, there may still remain a few reactions in cellular metabolism which are known to occur from in vitro assays and experimental data. These would include well characterized reactions for which a gene or protein has yet to be identified, or was unidentified from the genome sequencing and functional assignment of state 14 and 18. This would also include the transport of metabolites into or out of the cell by uncharacterized genes related to transport. Thus one reason for the missing gene information may be due to a lack of characterization of the actual gene that performs a known biochemical conversion. Therefore upon careful review of existing biochemical literature and available experimental data, additional metabolic reactions can be added to the list of metabolic reactions determined from the metabolic genotype from state 54 at a state 56. This would include information regarding the substrates, products, reversibility/irreversibility, and stoichiometry of the reactions.

All of the information obtained at states 54 and 56 regarding reactions and their stoichiometry can be represented in a matrix format typically referred to as a stoichiometric matrix. Each column in the matrix corresponds to a given reaction or flux, and each row corresponds to the different metabolites involved in the given reaction/flux. Reversible reactions may either be represented as one reaction that operates in both the forward and reverse direction or be decomposed into one forward reaction and one backward reaction in which case all fluxes can only take on positive values. Thus, a given position in the matrix describes the stoichiometric participation of a metabolite (listed in the given row) in a particular flux of interest (listed in the given column). Together all of the columns of the genome specific stoichiometric matrix represent all of the chemical conversions and cellular transport processes that are determined to be present in the organism. This includes all internal fluxes and so called exchange fluxes operating within the metabolic network. Thus, the process 50 moves to a state 58 in order to formulate all of the cellular reactions together in a genome specific stoichiometric matrix. The resulting genome specific stoichiometric matrix is a fundamental representation of a genomically and biochemically defined genotype.

After the genome specific stoichiometric matrix is defined at state 58, the metabolic demands placed on the organism are calculated. The metabolic demands can be readily determined from the dry weight composition of the cell. In the case of well-studied organisms such as *Escherichia coli* and *Bacillus subtilis*, the dry weight composition is available in the published literature. However, in some cases it will be necessary to experimentally determine the dry weight composition of the cell for the organism in question. This can be accomplished with varying degrees of accuracy. The first attempt would measure the RNA, DNA, protein, and lipid fractions of the cell. A more detailed analysis would also provide the specific fraction of nucleotides, amino acids, etc. The process 50 moves to state 60 for the determination of the biomass composition of the target organism.

The process 50 then moves to state 62 to perform several experiments that determine the uptake rates and maintenance requirements for the organism. Microbiological experiments can be carried out to determine the uptake rates for many of the metabolites that are transported into the cell. The uptake rate is determined by measuring the depletion of the substrate from the growth media. The measurement of the biomass at each point is also required, in order to determine the uptake rate per unit biomass. The maintenance requirements can be determined from a chemostat experiment. The glucose uptake rate is plotted versus the growth rate, and the y-intercept is interpreted as the non-growth associated maintenance requirements. The growth associated maintenance requirements are determined by fitting the model results to the experimentally determined points in the growth rate versus glucose uptake rate plot.

Next, the process 50 moves to a state 64 wherein information regarding the metabolic demands and uptake rates obtained at state 62 are combined with the genome specific stoichiometric matrix of step 8 together fully define the metabolic system using flux balance analysis (FBA). This is an approach well suited to account for genomic detail as it has been developed based on the well-known stoichiometry of metabolic reactions.

The time constants characterizing metabolic transients and/or metabolic reactions are typically very rapid, on the order of milli-seconds to seconds, compared to the time constants of cell growth on the order of hours to days. Thus, the transient mass balances can be simplified to only consider the steady state behavior. Eliminating the time derivatives obtained from dynamic mass balances around every metabolite in the metabolic system, yields the system of linear equations represented in matrix notation, $$S \cdot v = 0 \qquad \text{Equation 1}$$

where S refers to the stoichiometric matrix of the system, and v is the flux vector. This equation simply states that over long times, the formation fluxes of a metabolite must be balanced by the degradation fluxes. Otherwise, significant amounts of the metabolite will accumulate inside the metabolic network. Applying equation 1 to our system we let S now represent the genome specific stoichiometric matrix To determine the metabolic capabilities of a defined metabolic genotype Equation 1 is solved for the metabolic fluxes and the internal metabolic reactions, v, while imposing constraints on the activity of these fluxes. Typically the number of metabolic fluxes is greater than the number of mass balances (i.e., m>n) resulting in a plurality of feasible flux distributions that satisfy Equation 1 and any constraints placed on the fluxes of the system. This range of solutions is indicative of the flexibility in the flux distributions that can be achieved with a given set of metabolic reactions. The solutions to Equation 1 lie in a restricted region. This subspace defines the capabilities of the metabolic genotype of a given organism, since the allowable solutions that satisfy Equation 1 and any constraints placed on the fluxes of the system define all the metabolic flux distributions that can be achieved with a particular set of metabolic genes.

The particular utilization of the metabolic genotype can be defined as the metabolic phenotype that is expressed under those particular conditions. Objectives for metabolic function can be chosen to explore the 'best' use of the metabolic network within a given metabolic genotype. The solution to equation 1 can be formulated as a linear programming problem, in which the flux distribution that minimizes a particular objective if found. Mathematically, this optimization can be stated as;

$$\text{Minimize } Z \qquad \text{Equation 2}$$

$$\text{where } Z = \Sigma c_i \cdot v_i = <c \cdot v> \qquad \text{Equation 3}$$

where Z is the objective which is represented as a linear combination of metabolic fluxes $v_i$. The optimization can also be stated as the equivalent maximization problem; i.e. by changing the sign on Z.

This general representation of Z enables the formulation of a number of diverse objectives. These objectives can be design objectives for a strain, exploitation of the metabolic capabilities of a genotype, or physiologically meaningful objective functions, such as maximum cellular growth. For this application, growth is to be defined in terms of biosynthetic requirements based on literature values of biomass composition or experimentally determined values such as those obtained from state 60. Thus, we can define biomass generation as an additional reaction flux draining intermediate metabolites in the appropriate ratios and represented as an objective function Z. In addition to draining intermediate metabolites this reaction flux can be formed to utilize energy molecules such as ATP, NADH and NADPH so as to incorporate any maintenance requirement that must be met. This new reaction flux then becomes another constraint/balance equation that the system must satisfy as the objective function. It is analogous to adding an addition column to the stoichiometric matrix of Equation 1 to represent such a flux to describe the production demands placed on the metabolic system. Setting this new flux as the objective function and asking the system to maximize the value of this flux for a given set of constraints on all the other fluxes is then a method to simulate the growth of the organism.

Using linear programming, additional constraints can be placed on the value of any of the fluxes in the metabolic network.

$$\beta_j \le v_j \le \alpha_j \qquad \text{Equation 4}$$

These constraints could be representative of a maximum allowable flux through a given reaction, possibly resulting from a limited amount of an enzyme present in which case the value for $\alpha_j$ would take on a finite value. These constraints could also be used to include the knowledge of the minimum flux through a certain metabolic reaction in which case the value for $\beta_j$ would take on a finite value. Additionally, if one chooses to leave certain reversible reactions or transport fluxes to operate in a forward and reverse manner the flux may remain unconstrained by setting $\beta_j$ to negative infinity and $\alpha_j$ to positive infinity. If reactions proceed only in the forward reaction $\beta_j$ is set to zero while $\alpha_j$ is set to positive infinity. As an example, to simulate the event of a genetic deletion the flux through all of the corresponding metabolic reactions related to the gene in question are reduced to zero by setting $\beta_j$ and $\alpha_j$ to be zero in Equation 4. Based on the in vivo environment where the bacteria lives one can determine the metabolic resources available to the cell for biosynthesis of essentially molecules for biomass. Allowing the corresponding transport fluxes to be active provides the in silico bacteria with inputs and outputs for substrates and by-products produces by the metabolic network. Therefore as an example, if one wished to simulate the absence of a particular growth substrate one simply constrains the corresponding transport fluxes allowing the metabolite to enter the cell to be zero by allowing $\beta_j$ and $\alpha_j$ to be zero in Equation 4. On the other hand if a substrate is only allowed to enter or exit the cell via transport mechanisms, the corresponding fluxes can be properly constrained to reflect this scenario.

Together the linear programming representation of the genome-specific stoichiometric matrix as in Equation 1 along with any general constraints placed on the fluxes in the system, and any of the possible objective functions completes the formulation of the in silico bacterial strain. The in silico strain can then be used to study theoretical metabolic capabilities by simulating any number of conditions and generating flux distributions through the use of linear programming. The process 50 of formulating the in silico strain and simulating its behavior using linear programming techniques terminates at an end state 66.

Thus, by adding or removing constraints on various fluxes in the network it is possible to (1) simulate a genetic deletion event and (2) simulate or accurately provide the network with the metabolic resources present in its in vivo environment. Using flux balance analysis it is possible to determine the affects of the removal or addition of particular genes and their associated reactions to the composition of the metabolic genotype on the range of possible metabolic phenotypes. If the removal/deletion does not allow the metabolic network to produce necessary precursors for growth, and the cell can not obtain these precursors from its environment, the deletion(s) has the potential as an antimicrobial drug target. Thus by adjusting the constraints and defining the objective function we can explore the capabilities of the metabolic genotype using linear programming to optimize the flux distribution through the metabolic network. This creates what we will refer to as an in silico bacterial strain capable of being studied and manipulated to analyze, interpret, and predict the genotype-phenotype relationship. It can be applied to assess the affects of incremental changes in the genotype or changing environmental conditions, and provide a tool for computer aided experimental design. It should be realized that other types of organisms can similarly be represented in silico and still be within the scope of the invention.

The construction of a genome specific stoichiometric matrix and in silico microbial strains can also be applied to the area of signal transduction. The components of signaling networks can be identified within a genome and used to construct a content matrix that can be further analyzed using various techniques to be determined in the future.

EXAMPLE 1

A

E. coli Metabolic Genotype and In Silico Model

Using the methods disclosed in FIGS. 1 and 2, an in silico strain of Escherichia coli K-12 has been constructed and represents the first such strain of a bacteria largely generated from annotated sequence data and from biochemical information. The genetic sequence and open reading frame identifications and assignments are readily available from a number of on-line locations (ex: www.tigr.org). For this example we obtained the annotated sequence from the following website for the E. coli Genome Project at the University of Wisconsin. Details regarding the actual sequencing and annotation of the sequence can be found at that site. From the genome annotation data the subset of genes involved in cellular metabolism was determined as described above in FIG. 1, state 20, comprising the metabolic genotype of the particular strain of E. coli.

Through detailed analysis of the published biochemical literature on E. coli we determined (1) all of the reactions associated with the genes in the metabolic genotype and (2) any additional reactions known to occur from biochemical data which were not represented by the genes in the metabolic genotype. This provided all of the necessary information to construct the genome specific stoichiometric matrix for E. coli K-12.

Briefly, the E. coli K-12 bacterial metabolic genotype and more specifically the genome specific stoichiometric matrix contains 731 metabolic processes that influence 436 metabolites (dimensions of the genome specific stoichiometric matrix are 436×731). There are 80 reactions present in the genome specific stoichiometric matrix that do not have a genetic assignment in the annotated genome, but are known to be present from biochemical data. The genes contained within this metabolic genotype are shown in Table 1 along with the corresponding reactions they carry out.

Because E. coli is arguably the best studied organism, it was possible to determine the uptake rates and maintenance requirements (state 62 of FIG. 2) by reference to the published literature. This in silico strain accounts for the metabolic capabilities of E. coli. It includes membrane transport processes, the central catabolic pathways, utilization of alternative carbon sources and the biosynthetic pathways that generate all the components of the biomass. In the case of E. coli K-12, we can call upon the wealth of data on overall metabolic behavior and detailed biochemical information about the in vivo genotype to which we can compare the behavior of the in silico strain. One utility of FBA is the ability to learn about the physiology of the particular organism and explore its metabolic capabilities without any specific biochemical data. This ability is important considering possible future scenarios in which the only data that we may have for a newly discovered bacterium (perhaps pathogenic) could be its genome sequence.

EXAMPLE 2

B

In Silico Deletion Analysis for E. coli to Find Antimicrobial Targets

Using the in silico strain constructed in Example 1, the effect of individual deletions of all the enzymes in central metabolism can be examined in silico. For the analysis to determine sensitive linkages in the metabolic network of E. coli, the objective function utilized is the maximization of the biomass yield. This is defined as a flux draining the necessary biosynthetic precursors in the appropriate ratios. This flux is defined as the biomass composition, which can be determined from the literature. See Neidhardt et. al., Escherichia coli and Salmonella: Cellular and Molecular Biology, Second Edition, ASM Press, Washington D.C., 1996. Thus, the objective function is the maximization of a single flux, this biosynthetic flux.

Constraints are placed on the network to account for the availability of substrates for the growth of E. coli. In the initial deletion analysis, growth was simulated in an aerobic glucose minimal media culture. Therefore, the constraints are set to allow for the components included in the media to be taken up. The specific uptake rate can be included if the value is known, otherwise, an unlimited supply can be provided. The uptake rate of glucose and oxygen have been determined for E. coli (Neidhardt et. al., Escherichia coli and Salmonella: Cellular and Molecular Biology, Second Edition, ASM Press, Washington D.C., 1996. Therefore, these values are included in the analysis. The uptake rate for phosphate, sulfur, and nitrogen source is not precisely known, so constraints on the fluxes for the uptake of these important substrates is not included, and the metabolic network is allowed to take up any required amount of these substrates.

The results showed that a high degree of redundancy exists in central intermediary metabolism during growth in glucose minimal media, which is related to the interconnectivity of the metabolic reactions. Only a few metabolic functions were found to be essential such that their loss removes the capability of cellular growth on glucose. For growth on glucose, the essential gene products are involved in the 3-carbon stage of glycolysis, three reactions of the TCA cycle, and several points within the PPP. Deletions in the 6-carbon stage of glycolysis result in a reduced ability to support growth due to the diversion of additional flux through the PPP.

The results from the gene deletion study can be directly compared with growth data from mutants. The growth characteristics of a series of *E. coli* mutants on several different carbon sources were examined (80 cases were determined from the literature), and compared to the in silico deletion results (Table 2). The majority (73 of 80 cases or 91%) of the mutant experimental observations are consistent with the predictions of the in silico study. The results from the in silico gene deletion analysis are thus consistent with experimental observations.

EXAMPLE 3

C

Prediction of Genome Scale Shifts in Gene Expression

Flux based analysis can be used to predict metabolic phenotypes under different growth conditions, such as substrate and oxygen availability. The relation between the flux value and the gene expression levels is non-linear, resulting in bifurcations and multiple steady states. However, FBA can give qualitative (on/off) information as well as the relative importance of gene products under a given condition. Based on the magnitude of the metabolic fluxes, qualitative assessment of gene expression can be inferred.

Figures 3A, 3B, 3C:
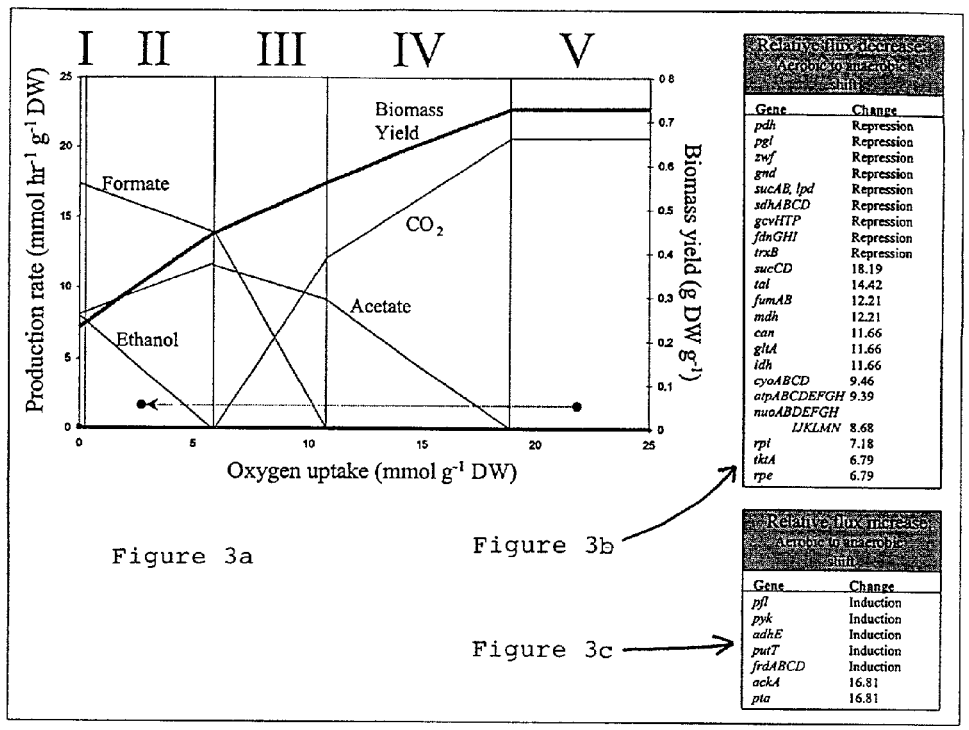
FIG. 3 is a graph illustrating a prediction of genome scale shifts in transcription. The graph shows the different phases of the metabolic response to varying oxygen availability, starting from completely aerobic to completely anaerobic in *E. coli*. The predicted changes in expression pattern between phases II and V are indicated.

FIG. 3a shows the five phases of distinct metabolic behavior of *E. coli* in response to varying oxygen availability, going from completely anaerobic (phase I) to completely aerobic (phase V). FIGS. 3b and 3c display lists of the genes that are predicted to be induced or repressed upon the shift from aerobic growth (phase V) to nearly complete anaerobic growth (phase II). The numerical values shown in FIGS. 3b and 3c are the fold change in the magnitude of the fluxes calculated for each of the listed enzymes.

For this example, the objective of maximization of biomass yield is utilized (as described above). The constraints on the system are also set accordingly (as described above). However, in this example, a change in the availability of a key substrate is leading to changes in the metabolic behavior. The change in the parameter is reflected as a change in the uptake flux. Therefore, the maximal allowable oxygen uptake rate is changed to generate this data. The figure demonstrates how several fluxes in the metabolic network will change as the oxygen uptake flux is continuously decreased. Therefore, the constraints on the fluxes is identical to what is described in the previous section, however, the oxygen uptake rate is set to coincide with the point in the diagram.

Corresponding experimental data sets are now becoming available. Using high-density oligonucleotide arrays the expression levels of nearly every gene in *Saccharomyces cerevisiae* can now be analyzed under various growth conditions. From these studies it was shown that nearly 90% of all yeast mRNAs are present in growth on rich and minimal media, while a large number of mRNAs were shown to be differentially expressed under these two conditions. Another recent article shows how the metabolic and genetic control of gene expression can be studied on a genomic scale using DNA microarray technology (Exploring the Metabolic and Genetic Control of Gene Expression on a Genomic Scale, *Science*, Vol. 278, Oct. 24, 1997. The temporal changes in genetic expression profiles that occur during the diauxic shift in *S. cerevisiae* were observed for every known expressed sequence tag (EST) in this genome. As shown above, FBA can be used to qualitatively simulate shifts in metabolic genotype expression patterns due to alterations in growth environments. Thus, FBA can serve to complement current studies in metabolic gene expression, by providing a fundamental approach to analyze, interpret, and predict the data from such experiments.

EXAMPLE 4

D

Design of Defined Media

An important economic consideration in large-scale bioprocesses is optimal medium formulation. FBA can be used to design such media. Following the approach defined above, a flux-balance model for the first completely sequenced free living organism, *Haemophilus influenzae*, has been generated. One application of this model is to predict a minimal defined media. It was found that *H. influenzae* can grow on the minimal defined medium as determined from the ORF assignments and predicted using FBA. Simulated bacterial growth was predicted using the following defined media: fructose, arginine, cysteine, glutamate, putrescine, spermidine, thiamin, NAD, tetrapyrrole, pantothenate, ammonia, phosphate. This predicted minimal medium was compared to the previously published defined media and was found to differ in only one compound, inosine. It is known that inosine is not required for growth, however it does serve to enhance growth. Again the in silico results obtained were consistent with published in vivo research. These results provide confidence in the use of this type of approach for the design of defined media for organisms in which there currently does not exist a defined media.

While particular embodiments of the invention have been described in detail, it will be apparent to those skilled in the art that these embodiments are exemplary rather than limiting, and the true scope of the invention is defined by the claims that follow.

TABLE 1

The genes included in the *E. coli* metabolic genotype along with corresponding enzymes and reactions that comprise the genome specific stoichiometric matrix. The final column indicates the presence/absence of the gene (as the number of copies) in the *E. coli* genome. Thus the presence of a gene in the *E. coli* genome indicates that the gene is part of the metabolic genotype. Reactions/Genes not present in the genome are those gathered at state 56 in FIG. 2 and together with the reactions of the genes in the metabolic genotype form the columns of the genome specific stoichiometric matrix.

| Enzyme | Gene | Reaction | E. coli Genome |
|---|---|---|---|
| Glucokinase | glk | GLC + ATP -> G6P + ADP | 1 |
| Glucokinase | glk | bDGLC + ATP -> bDG6P + ADP | 1 |
| Phosphoglucose isomerase | pgi | G6P <-> F6P | 1 |
| Phosphoglucose isomerase | pgi | bDG6P <-> G6P | 1 |
| Phosphoglucose isomerase | pgi | bDG6P <-> F6P | 1 |
| Aldose 1-epimerase | galM | bDGLC <-> GLC | 1 |
| Glucose-1-phophatase | agp | G1P -> GLC + PI | 1 |
| Phosphofructokinase | pfk4 | F6P + ATP -> FDP + ADP | 1 |

TABLE 1-continued

The genes included in the E. coli metabolic genotype along with corresponding enzymes and reactions that comprise the genome specific stoichiometric matrix. The final column indicates the presence/absence of the gene (as the number of copies) in the E. coli genome. Thus the presence of a gene in the E. coli genome indicates that the gene is part of the metabolic genotype. Reactions/Genes not present in the genome are those gathered at state 56 in FIG. 2 and together with the reactions of the genes in the metabolic genotype form the columns of the genome specific stoichiometric matrix.

| Enzyme | Gene | Reaction | E. coli Genome |
|---|---|---|---|
| Phosphofructokinase B | pfkB | F6P + ATP -> FDP + ADP | 1 |
| Fructose-1,6-bisphosphatase | fbp | FDP -> F6P + PI | 1 |
| Fructose-1,6-bisphosphatate aldolase | fba | FDP <-> T3P1 + T3P2 | 2 |
| Triosphosphate Isomerase | tpiA | T3P1 <-> T3P2 | 1 |
| Methylglyoxal synthase | mgsA | T3P2 -> MTHGXL + PI | 0 |
| Glyceraldehyde-3-phosphate dehydrogenase-A complex | gapA | T3P1 + PI + NAD <-> NADH + 13PDG | 1 |
| Glyceraldehyde-3-phosphate dehydrogenase-C complex | gapC1C2 | T3P1 + PI + NAD <-> NADH + 13PDG | 2 |
| Phosphoglycerate kinase | pgk | 13PDG + ADP <-> 3PG + ATP | 1 |
| Phosphoglycerate mutase 1 | gpmA | 3PG <-> 2PG | 1 |
| Phosphoglycerate mutase 2 | gpmB | 3PG <-> 2PG | 1 |
| Enolase | eno | 2PG <-> PEP | 1 |
| Phosphoenolpyruvate synthase | ppsA | PYR + ATP -> PEP + AMP + PI | 1 |
| Pyruvate Kinase II | pykA | PEP + ADP -> PYR + ATP | 1 |
| Pyruvate Kinase I | pykF | PEP + ADP -> PYR + ATP | 1 |
| Pyruvate dehydrogenase | lpdA, aceEF | PYR + COA + NAD -> NADH + CO2 + ACCOA | 3 |
| Glucose-1-phosphate adenylyltransferase | glgC | ATP + G1P -> ADPGLC + PPI | 1 |
| Glycogen synthase | glgA | ADPGLC -> ADP + GLYCOGEN | 1 |
| Glycogen phosphorylase | glgP | GLYCOGEN + PI -> G1P | 1 |
| Maltodextrin phosphorylase | malP | GLYCOGEN + PI -> G1P | 1 |
| Glucose 6-phosphate-1-dehydrogenase | zwf | G6P + NADP <-> D6PGL + NADPH | 1 |
| 6-Phosphogluconolactonase | pgl | D6PGL -> D6PGC | 0 |
| 6-Phosphogluconate dehydrogenase (decarboxylating) | gnd | D6PGC + NADP -> NADPH + CO2 + RL5P | 1 |
| Ribose-5-phosphate isomerase A | rpiA | RL5P <-> R5P | 1 |
| Ribose-5-phosphate isomerase B | rpiB | RL5P <-> R5P | 1 |
| Ribulose phosphate 3-epimerase | rpe | RL5P <-> X5P | 1 |
| Transketolase I | tktA | R5P + X5P <-> T3P1 + S7P | 1 |
| Transketolase II | tktB | R5P + X5P <-> T3P1 + S7P | 1 |
| Transketolase I | tktA | X5P + E4P <-> F6P + T3P1 | 1 |
| Transketolase II | tktB | X5P + E4P <-> F6P + T3P1 | 1 |
| Transaldolase B | talB | T3P1 + S7P <-> E4P + F6P | 1 |
| Phosphogluconate dehydratase | edd | D6PGC -> 2KD6PG | 1 |
| 2-Keto-3-deoxy-6-phosphogluconate aldolase | eda | 2KD6PG -> T3P1 + PYR | 1 |
| Citrate synthase | gltA | ACCOA + OA -> COA + CIT | 1 |
| Aconitase A | acnA | CIT <-> ICIT | 1 |
| Aconitase B | acnB | CIT <-> ICIT | 1 |
| Isocitrate dehydrogenase | icdA | ICIT + NADP <-> CO2 + NADPH + AKG | 1 |
| 2-Ketoglutarate dehyrogenase | sucAB, lpdA | AKG + NAD + COA -> CO2 + NADH + SUCCOA | 3 |
| Succinyl-CoA synthetase | sucCD | SUCCOA + ADP + PI <-> ATP + COA + SUCC | 2 |
| Succinate dehydrogenase | sdhABCD | SUCC + FAD -> FADH + FUM | 4 |
| Fumurate reductase | frdABCD | FUM + FADH -> SUCC + FAD | 4 |
| Fumarase A | fumA | FUM <-> MAL | 1 |
| Fumarase B | fumB | FUM <-> MAL | 1 |
| Fumarase C | fumC | FUM <-> MAL | 1 |
| Malate dehydrogenase | mdh | MAL + NAD <-> NADH + OA | 1 |
| D-Lactate dehydrogenase 1 | dld | PYR + NADH <-> NAD + LAC | 1 |
| D-Lactate dehydrogenase 2 | ldhA | PYR + NADH <-> NAD + LAC | 1 |
| Acetaldehyde dehydrogenase | adhE | ACCOA + 2 NADH <-> ETH + 2 NAD + COA | 1 |
| Pyruvate formate lyase 1 | pflAB | PYR + COA -> ACCOA + FOR | 2 |
| Pyruvate formate lyase 2 | pflCD | PYR + COA -> ACCOA + FOR | 2 |
| Formate hydrogen lyase | fdhF, hycBEFG | FOR -> CO2 | 5 |
| Phosphotransacetylase | pta | ACCOA + PI <-> ACTP + COA | 1 |
| Acetate kinase A | ackA | ACTP + ADP <-> ATP + AC | 1 |
| GAR transformylase T | purT | ACTP + ADP <-> ATP + AC | 1 |
| Acetyl-CoA synthetase | acs | ATP + AC + COA -> AMP + PPI + ACCOA | 1 |
| Phosphoenolpyruvate carboxykinase | pckA | OA + ATP -> PEP + CO2 + ADP | 1 |
| Phosphoenolpyruvate carboxylase | ppc | PEP + CO2 -> OA + P1 | 1 |
| Malic enzyme (NADP) | maeB | MAL + NADP -> CO2 + NADPH + PYR | 0 |
| Malic enzyme (NAD) | sfcA | MAL + NAD -> CO2 + NADH + PYR | 1 |
| Isocitrate lyase | aceA | ICIT -> GLX + SUCC | 1 |
| Malate synthase A | aceB | ACCOA + GLX -> COA + MAL | 1 |
| Malate synthase G | glcB | ACCOA + GLX -> COA + MAL | 1 |
| Inorganic pyrophosphatase | ppa | PPI -> 2 PI | 1 |
| NAPIT dehydrogenase II | ndh | NADH + Q -> NAD + QH2 | 1 |
| NADH dehydrogenase I | nuoABEFGHIJ | NADH + Q -> NAD + QH2 + 3.5 HEXT | 1 |
| Formate dehydrogenase-N | fdnGHI | FOR + Q -> QH2 + CO2 + 2 HEXT | 3 |
| Formate dehydrogenase-O | fdoIHG | FOR + Q -> QH2 + CO2 + 2 HEXT | 3 |
| Formate dehydrogenase | fdhF | FOR + Q -> QH2 + CO2 + 2 HEXT | 1 |
| Pyruvate oxidase | poxB | PYR + Q -> AC + CO2 + QH2 | 1 |
| Glycerol-3-phosphate dehydrogenase (aerobic) | glpD | GL3P + Q -> T3P2 + QH2 | 1 |
| Glycerol-3-phosphate dehydrogenase (anaerobic) | glpABC | GL3P + Q -> T3P2 + QH2 | 3 |
| Cytochrome oxidase bo3 | cyoABCD, cyc | QH2 + .5 O2 -> Q + 2.5 HEXT | 6 |

TABLE 1-continued

The genes included in the E. coli metabolic genotype along with corresponding enzymes and reactions that comprise the genome specific stoichiometric matrix. The final column indicates the presence/absence of the gene (as the number of copies) in the E. coli genome. Thus the presence of a gene in the E. coli genome indicates that the gene is part of the metabolic genotype. Reactions/Genes not present in the genome are those gathered at state 56 in FIG. 2 and together with the reactions of the genes in the metabolic genotype form the columns of the genome specific stoichiometric matrix.

| Enzyme | Gene | Reaction | E. coli Genome |
|---|---|---|---|
| Cytochrome oxidase bd | cydABCD, app | QH2 + .5 O2 -> Q + 2 HEXT | 6 |
| Succinate dehydrogenase complex | sdhABCD | FADH + Q <-> FAD + QH2 | 4 |
| Thioredoxin reductase | trxB | OTHIO + NADPH -> NADP + RTHIO | 1 |
| Pyridine nucleotide transhydrogenase | pntAB | NADPH + NAD -> NADP + NADH | 2 |
| Pyridine nucleotide transhydrogenase | pntAB | NADP + NADH + 2 HEXT -> NADPH + NAD | 2 |
| Hydrogenase 1 | hyaABC | 2 Q + 2 HEXT <-> 2 QH2 + H2 | 3 |
| Hydrogenase 2 | hybAC | 2 Q + 2 HEXT <-> 2 QH2 + H2 | 2 |
| Hydrogenase 3 | hycFGBE | 2 Q + 2 HEXT <-> 2 QH2 + H2 | 4 |
| F0F1-ATPase | atpABCDEFG | ATP <-> ADP + PI + 4 HEXT | 9 |
| Alpha-galactosidase (melibiase) | melA | MELI -> GLC + GLAC | 1 |
| Galactokinase | galK | GLAC + ATP -> GAL1P + ADP | 1 |
| Galactose-1-phosphate uridylyltransferase | galT | GAL1P + UDPG <-> G1P + UDPGAL | 1 |
| UDP-glucose 4-epimerase | galE | UDPGAL <-> UDPG | 1 |
| UDP-glucose-1-phosphate uridylyltransferase | galU | G1P + UTP <-> UDPG + PPI | 1 |
| Phosphoglucomutase | pgm | G1P <-> G6P | 1 |
| Periplasmic beta-glucosidase precursor | bglX | LCTS -> GLC + GLAC | 1 |
| Beta-galactosidase (LACTase) | lacZ | LCTS -> GLC + GLAC | 1 |
| trehalose-6-phosphate hydrolase | treC | TRE6P -> bDG6P + GLC | 1 |
| Beta-fructofuranosidase | | SUC6P -> G6P + FRU | 0 |
| 1-Phosphofructokinase (Fructose 1-phosphate kinase) | fruK | F1P + ATP -> FDP + ADP | 1 |
| Xylose isomerase | xylA | FRU -> GLC | 1 |
| Phosphomannomutase | cpsG | MAN6P <-> MAN1P | 1 |
| Mannose-6-phosphate isomerase | manA | MACN1P <-> F6P | 1 |
| N-Acetylglucosamine-6-phosphate deacetylase | nagA | NAGP -> GA6P + AC | 1 |
| Glucosamine-6-phosphate deaminase | nagB | GA6P -> F6P + NH3 | 1 |
| N-Acetylneuraminate lyase | nanA | SLA -> PYR + NAMAN | 1 |
| L-Fucose isomerase | fucI | FUC <-> FCL | 1 |
| L-Fuculokinase | fucK | FCL + ATP -> FCL1P + ADP | 1 |
| L-Fuculose phosphate aldolase | fucA | FCL1P <-> LACAL + T3P2 | 1 |
| Lactaldehyde reductase | fucO | LACAL + NADH <-> 12PPD + NAD | 1 |
| Aldehyde dehydrogenase A | aldA | LACAL + NAD <-> LLAC + NADH | 1 |
| Aldehyde dehydrogenase B | aldB | LACAL + NAD <-> LLAC + NADH | 1 |
| Aldehyde dehydrogenase | adhC | LACAL + NAD <-> LLAC + NADH | 1 |
| Aldehyde dehydrogenase | adhC | GLAL + NADH <-> GL + NADH | 1 |
| Aldehyde dehydrogenase | adhE | LACAL + NAD -> LLAC + NADH | 1 |
| Aldehyde dehydrogenase | aldH | LACAL + NAD <-> LLAC + NADH | 1 |
| Aldehyde dehydrogenase | aldH | ACAL + NAD -> AC + NADH | 1 |
| Gluconokinase I | gntV | GLCN + ATP -> D6PGC + ADP | 1 |
| Gluconokinase II | gntK | GLCN + ATP -> D6PGC + ADP | 1 |
| L-Rhamnose isomerase | rhaA | RMN <-> RML | 1 |
| Rhamnulokinase | rhaB | RML + ATP -> RML1P + ADP | 1 |
| Rhamnulose-1-phosphate aldolase | rhaD | RML1P <-> LACAL + T3P2 | 1 |
| L-Arabinose isomerase | araA | ARAB <-> RBL | 1 |
| Arabinose-5-phospliate isomerase | | RL5P <-> A5P | 0 |
| L-Ribulokinase | araB | RBL + ATP -> RL5P + ADP | 1 |
| L-Ribulose-phosphate 4-epimerase | araD | RL5P <-> X5P | 1 |
| Xylose isomerase | xylA | XYL <-> XUL | 1 |
| Xylulokinase | xylB | XUL + ATP -> X5P + ADP | 1 |
| Ribokinase | rbsK | RIB + ATP -> R5P + ADP | 1 |
| Mannitol-1-phosphate 5-dehydrogenase | mtlD | MNT6P + NAD <-> F6P + NADH | 1 |
| Glucitol-6-phosphate dehydrogenase | srlD | GLT6P + NAD <-> F6P + NADH | 1 |
| Galactitol-1-phosphate dehydrogenase | gatD | GLTL1P + NAD <-> TAG6P + NADH | 1 |
| Phosphofructokinase B | pfkB | TAG6P + ATP -> TAG16P + ADP | 1 |
| 1-Phosphofructokinase | fruK | TAG6P + ATP -> TAG16P + ADP | 1 |
| Tagatose-6-phosphate kinase | agaZ | TAG6P + ATP -> TAG16P + ADP | 1 |
| Tagatose-bisphosphate aldolase 2 | gatY | TAG16P <-> T3P2 + T3P1 | 1 |
| Tagatose-bisphosphate aldolase 1 | agaY | TAG16P <-> T3P2 + T3P1 | 1 |
| Glycerol kinase | glpK | GL + ATP -> GL3P + ADP | 1 |
| Glycerol-3-phosphate-dehydrogenase-[NAD(P)+] | gpsA | GL3P + NADP <-> T3P2 + NADPH | 1 |
| Phosphopentomutase | deoB | DR1P <-> DR5P | 1 |
| Phosphopentomutase | deoB | R1P <-> R5P | 1 |
| Deoxyribose-phosphate aldolase | deoC | DR5P -> ACAL + T3P1 | 1 |
| Asparate transaminase | aspC | OA + GLU <-> ASP + AKG | 1 |
| Asparagine synthetase (Glutamate dependent) | asnB | ASP + ATP + GLN -> GLU + ASN + AMP + PPI | 1 |
| Aspartate-ammonia ligase | asnA | ASP + ATP + NH3 -> ASN + AMP + PPI | 1 |
| Glutamate dehydrogenase | gdhA | AKG + NH3 + NADPH <-> GLU + NADP | 1 |
| Glutamate-ammonia ligase | glnA | GLU + NH3 + ATP -> GLN + ADP + PI | 1 |
| Glutamate synthase | gltBD | AKG + GLN + NADPH -> NADP + 2 GLU | 2 |
| Alanine transaminase | alaB | PYR + GLU <-> AKG + ALA | 0 |
| Valine-pyruvate aminotransferase | avtA | OIVAL + ALA -> PYR + VAL | 1 |
| Alanine racemase, biosynthetic | alr | ALA <-> DALA | 1 |

TABLE 1-continued

The genes included in the *E. coli* metabolic genotype along with corresponding enzymes and reactions that comprise the genome specific stoichiometric matrix. The final column indicates the presence/absence of the gene (as the number of copies) in the *E. coli* genome. Thus the presence of a gene in the *E. coli* genome indicates that the gene is part of the metabolic genotype. Reactions/Genes not present in the genome are those gathered at state 56 in FIG. 2 and together with the reactions of the genes in the metabolic genotype form the columns of the genome specific stoichiometric matrix.

| Enzyme | Gene | Reaction | *E. coli* Genome |
|---|---|---|---|
| Alanine racemase, catabolic | dadX | ALA -> DALA | 1 |
| N-Acetylglutamate synthase | argA | GLU + ACCOA -> COA + NAGLU | 1 |
| N-Acetylglutamate kinase | argB | NAGLU + ATP -> ADP + NAGLUYP | 1 |
| N-Acetylglutamate phosphate reductase | argC | NAGLUYP + NADPH <-> NADP + PI + NAGLUSAL | 1 |
| Acetylornithine transaminase | argD | NAGLUSAL + GLU <-> AKG + NAARON | 1 |
| Acetylornithine deacetylase | argE | NAARON -> AC + ORN | 1 |
| Carbamoyl phosphate synthetase | carAB | GLN + 2 ATP + CO2 -> GLU + CAP + 2 ADP + PI | 2 |
| Ornithine carbamoyl transferase 1 | argF | ORN + CAP <-> CITR + PI | 2 |
| Ornithine carbamoyl transferase 2 | argI | ORN + CAP <-> CITR + PI | 1 |
| Ornithine transaminase | ygjGH | ORN + AKG -> GLUGSAL + GLU | 2 |
| Argininosuccinate synthase | argG | CITR + ASP + ATP -> AMP + PPI + ARGSUCC | 1 |
| Argininosuccinate lyase | argH | ARGSUCC <-> FUM + ARG | 1 |
| Arginine decarboxylase, biosynthetic | speA | ARG -> CO2 + AGM | 1 |
| Arginine decarboxylase, degradative | adi | ARG -> CO2 + AGM | 1 |
| Agmatinase | speB | AGM -> UREA + PTRC | 1 |
| Ornithine decarboxylase, biosynthetic | speC | ORN -> PTRC + CO2 | 1 |
| Ornithine decarboxylase, degradative | speF | ORN -> PTRC + CO2 | 1 |
| Adenosylmethionine decarboxylase | speD | SAM <-> DSAM + CO2 | 1 |
| Spermidine synthase | speE | PTRC + DSAM -> SPMD + 5MTA | 1 |
| Methylthioadenosine nucleosidase | | 5MTA -> AD + 5MTR | 0 |
| 5-Methylthioribose kinase | | 5MTR + ATP -> 5MTRP + ADP | 0 |
| 5-Methylthioribose-1-phosphate isomerase | | 5MTRP <-> 5MTR1P | 0 |
| E-1 (Enolase-phosphatase) | | 5MTR1P -> DKMPP | 0 |
| E-3 (Unknown) | | DKMPP -> FOR + KMB | 0 |
| Transamination (Unknown) | | KMB + GLN -> GLU + MET | 0 |
| γ-Glutamyl kinase | proB | GLU + ATP -> ADP + GLUP | 1 |
| Glutamate-5-semialdehyde dehydrogenase | proA | GLUP + NADPH -> NADP + PI + GLUGSAL | 1 |
| N-Acetylornithine deacetylase | argE | NAGLUSAL -> GLUGSAL + AC | 1 |
| Pyrroline-5-carboxylate reductase | proC | GLUGSAL + NADPH -> PRO + NADP | 1 |
| Threonine dehydratase, biosynthetic | ilvA | THR -> NH3 + OBUT | 1 |
| Threonine dehydratase, catabolic | tdcB | THR -> NH3 + OBUT | 1 |
| Acetohydroxybutanoate synthase I | ilvBN | OBUT + PYR -> ABUT + CO2 | 2 |
| Acetohydroxybutanoate synthase II | ilvG(12)M | OBUT + PYR -> ABUT + CO2 | 3 |
| Acetohydroxybutanoate synthase III | ilvIH | OBUT + PYR -> ABUT + CO2 | 2 |
| Acetohydroxy Acid isomeroreductase | ilvC | ABUT + NADPH -> NADP + DHMVA | 1 |
| Dihydroxy acid dehydratase | ilvD | DHMVA -> OMVAL | 1 |
| Branched chain amino acid aminotransferase | ilvE | OMVAL + GLU <-> AKG + ILE | 1 |
| Acetolactate synthase I | ilvBN | 2 PYR -> CO2 + ACLAC | 2 |
| Acetolactate synthase II | ilvG(12)M | 2 PYR -> CO2 + ACLAC | 3 |
| Acetolactate synthase III | ilvIH | 2 PYR -> CO2 + ACLAC | 2 |
| Acetohydroxy acid isomeroreductase | ilvC | ACLAC + NADPH -> NADP + DHVAL | 1 |
| Dihydroxy acid dehydratase | ilvD | DHVAL -> OIVAL | 1 |
| Branched chain amino acid aminotransferase | ilvE | OIVAL + GLU -> AKG + VAL | 1 |
| Valine-pyruvate aminotransferase | avtA | OIVAL + ALA -> PYR + VAL | 1 |
| Isopropylmalate synthase | leuA | ACCOA + OLVAL -> COA + CBHCAP | 1 |
| Isopropylmalate isomerase | leuCD | CBHCAP <-> IPPMAL | 2 |
| 3-Isopropylmalate dehydrogenase | leuB | IPPMAL + NAD -> NADH + OICAP + CO2 | 1 |
| Branched chain amino acid aminotransferase | ilvE | OICAP + GLU -> AKG + LEU | 1 |
| Aromatic amino acid transaminase | tyrB | OICAP + GLU -> AKG + LEU | 1 |
| 2-Dehydro-3-deoxyphosphoheptonate aldolase F | aroF | E4P + PEP -> PI + 3DDAH7P | 1 |
| 2-Dehydro-3-deoxyphosphoheptonate aldolase G | aroG | E4P + PEP -> PI + 3DDAH7P | 1 |
| 2-Dehydro-3-deoxyphosphoheptonate aldolase H | aroH | E4P + PEP -> PI + 3DDAH7P | 1 |
| 3-Dehydroquinate synthase | aroB | 3DDAH7P -> DQT + PI | 1 |
| 3-Dehydroquinate dehydratase | aroD | DQT <-> DHSK | 1 |
| Shikimate dehydrogenase | aroE | DHSK + NADPH <-> SME + NADP | 1 |
| Shikimate kinase I | aroK | SME + ATP -> ADP + SME5P | 1 |
| Shikimate kinase II | aroL | SME + ATP -> ADP + SME5P | 1 |
| 3-Phosphoshikimate-1-carboxyvinyltransferase | aroA | SME5P + PEP <-> 3PSME + PI | 1 |
| Chorismate synthase | aroC | 3PSME -> PI + CHOR | 1 |
| Chorismate mutase 1 | pheA | CHOR -> PHEN | 1 |
| Prephenate dehydratase | pheA | PHEN -> CO2 + PHPYR | 1 |
| Aromatic amino acid transaminase | tyrB | PHPYR + GLU <-> AKG + PHE | 1 |
| Chorismate mutase 2 | tyrA | CHOR -> PHEN | 1 |
| Prephanate dehydrogenase | tyrA | PHEN + NAD -> HPHPYR + CO2 + NADH | 1 |
| Aromatic amino acid transaminase | tyrB | HPHPYR + GLU <-> AKG + TYR | 1 |
| Asparate transaminase | aspC | HPHPYR + GLU <-> AKG + TYR | 1 |
| Anthranilate synthase | trpDE | CHOR + GLN -> GLU + PYR + AN | 2 |
| Anthranilate synthase component II | trpD | AN + PRPP -> PPI + NPRAN | 1 |
| Phosphoribosyl anthranilate isomerase | trpC | NPRAN -> CPAD5P | 1 |
| Indoleglycerol phosphate synthase | trpC | CPAD5P -> CO2 + IGP | 1 |
| Tryptophan synthase | trpAB | IGP + SER -> T3P1 + TRP | 2 |

TABLE 1-continued

The genes included in the E. coli metabolic genotype along with corresponding enzymes and reactions that comprise the genome specific stoichiometric matrix. The final column indicates the presence/absence of the gene (as the number of copies) in the E. coli genome. Thus the presence of a gene in the E. coli genome indicates that the gene is part of the metabolic genotype. Reactions/Genes not present in the genome are those gathered at state 56 in FIG. 2 and together with the reactions of the genes in the metabolic genotype form the columns of the genome specific stoichiometric matrix.

| Enzyme | Gene | Reaction | E. coli Genome |
|---|---|---|---|
| Pliosphoribosyl pyrophosphate synthase | prsA | R5P + ATP <-> PRPP + AMP | 1 |
| ATP phosphoribosyltransferase | hisG | PRPP + ATP -> PPI + PRBATP | 1 |
| Phosphoribosyl-ATP pyrophosphatase | hisIE | PRBATP -> PPI + PRBAMP | 1 |
| Phosphoribosyl-AMP cyclohydrolase | hisIE | PRBAMP -> PRFP | 1 |
| Phosphoribosylformimino-5-amino-1-phosphonbosyl-4-imidazole c | hisA | PRFP -> PRLP | 1 |
| Imidazoleglycerol phosphate synthase | hisFH | PRLP + GLN -> GLU + AICAR + DIMGP | 2 |
| Imidazoleglycerol phosphate dehydratase | hisB | DIMGP -> IMACP | 1 |
| L-Histidinol phosphate aminotransferase | hisC | IMACP + GLU -> AKG + HISOLP | 1 |
| Histidinol phosphatase | hisB | HISOLP -> PI + HISOL | 1 |
| Histidinol dehydrogenase | hisD | HISOL + 3 NAD -> HIS + 3 NADH | 1 |
| 3-Phosphoglycerate dehydrogenase | serA | 3PG + NAD -> NADH + PHP | 1 |
| Phosphoserine transaminase | serC | PHP + GLU -> AKG + 3PSER | 1 |
| Phosphoserine phosphatase | serB | 3PSER -> PI + SER | 1 |
| Glycine hydroxymethyltransferase | glyA | THF + SER -> GLY + METTHF | 1 |
| Threonine dehydrogenase | tdh | THR + COA -> GLY + ACCOA | 1 |
| Amino ketobutyrate CoA ligase | kbl | THR + COA -> GLY + ACCOA | 1 |
| Sulfate adenylyltransferase | cysDN | SLF + ATP + GTP -> PPI + APS + GDP + PI | 2 |
| Adenylylsulfate kinase | cysC | APS + ATP -> ADP + PAPS | 1 |
| 3'-Phospho-adenylylsulfate reductase | cysH | PAPS + RTHIO -> OTHIO + H2SO3 + PAP | 1 |
| Suffite reductase | cysIJ | H2SO3 + 3NADPH <-> H2S + 3 NADP | 2 |
| Serine transacetylase | cysE | SER + ACCOA <-> COA + ASER | 1 |
| O-Acetylserine (thiol)-lyase A | cysK | ASER + H2S -> AC + CYS | 1 |
| O-Acetylserine (thiol)-lyase B | cysM | ASER + H2S -> AC + CYS | 1 |
| 3'-5' Bisphosphate nucleotidase | | PAP -> AMP + PI | 0 |
| Aspartate kinase I | thrA | ASP + ATP <-> ADP + BASP | 1 |
| Aspartate kinase II | metL | ASP + ATP <-> ADP + BASP | 1 |
| Aspartate kinase III | lysC | ASP + ATP <-> ADP + BASP | 1 |
| Aspartate semialdehyde dehydrogenase | asd | BASP + NADPH <-> NADP + PI + ASPSA | 1 |
| Homoserine dehydrogenase I | thrA | ASPSA + NADPH <-> NADP + HSER | 1 |
| Homoserine dehydrogenase II | metL | ASPSA + NADPH <-> NADP + HSER | 1 |
| Homoserine kinase | thrB | HSER + ATP -> ADP + PHSER | 1 |
| Threonine synthase | thrC | PHSER -> PI + THR | 1 |
| Dihydrodipicolinate synthase | dapA | ASPSA + PYR -> D23PIC | 1 |
| Dihydrodipicolinate reductase | dapB | D23PIC + NADPH -> NADP + PIP26DX | 1 |
| Tetrahydrodipicolinate succinylase | dapD | PIP26DX + SUCCOA -> COA + NS2A6O | 1 |
| Succinyl diaminopimelate aminotransferase | dapC | NS2A6O + GLU <-> AKG + NS26DP | 0 |
| Succinyl diaminopimelate desuccinylase | dapE | NS26DP -> SUCC + D26PIM | 1 |
| Diaminopimelate epimerase | dapF | D26PIM <-> MDAP | 1 |
| Diaminopimelate decarboxylase | lysA | MDAP -> CO2 + LYS | 1 |
| Lysine decarboxylase 1 | cadA | LYS -> CO2 + CADV | 1 |
| Lysine decarboxylase 2 | ldcC | LYS -> CO2 + CADV | 1 |
| Homoserine transsuccinylase | metA | HSER + SUCCOA -> COA + OSLHSER | 1 |
| O-succinylhomoserine lyase | metB | OSLHSER + CYS -> SUCC + LLCT | 1 |
| Cystathionine-β-lyase | metC | LLCT -> HCYS + PYR + NH3 | 1 |
| Adenosyl homocysteinase (Unknown) | Unknown | HCYS + ADN <-> SAH | 0 |
| Cobalamin-dependent methionine synthase | metH | HCYS + MTHF -> MET + THF | 1 |
| Cobalamin-independent methionine synthase | metE | HCYS + MTHF -> MET + THF | 1 |
| 5-Adenosylmethionine synthetase | metK | MET + ATP -> PPI + PI + SAM | 1 |
| D-Amino acid dehydrogenase | dadA | DALA + FAD -> FADH + PYR + NH3 | 1 |
| Putrescine transaminase | pat | PTRC + AKG -> GABAL + GLU | 0 |
| Amino oxidase | tynA | PTRC -> GABAL + NH3 | 1 |
| Aminobutyraldehyde dehydrogenase | prr | GABAL + NAD -> GABA + NADH | 0 |
| Aldehyde dehydrogenase | aldH | GABAL + NAD -> GABA + NADH | 1 |
| Aminobutyrate aminotransaminase 1 | gabT | GABA + AKG -> SUCCSAL + GLU | 1 |
| Aminobutyrate aminotransaminase 2 | goaG | GABA + AKG -> SUCCSAL + GLU | 1 |
| Succinate semialdehyde dehydrogenase-NAD | sad | SUCCSAL + NAD -> SUCC + NADH | 0 |
| Succinate semialdehyde dehydrogenase-NADP | gabD | SUCCSAL + NADP -> SUCC + NADPH | 1 |
| Asparininase I | ansA | ASN -> ASP + NH3 | 1 |
| Asparininase II | ansB | ASN -> ASP + NH3 | 1 |
| Aspartate ainmonia-lyase | aspA | ASP -> FUM + NH3 | 1 |
| Tryptophanase | tnaA | CYS -> PYR + NH3 + H2S | 1 |
| L-Cysteine desulfhydrase | | CYS -> PYR + NH3 + H2S | 0 |
| Glutamate decarboxylase A | gadA | GLU -> GABA + CO2 | 1 |
| Glutamate decarboxylase B | gadB | GLU -> GABA + CO2 | 1 |
| Glutaminase A | | GLN -> GLU + NH3 | 0 |
| Glutaminase B | | GLN -> GLU + NH3 | 0 |
| Proline dehydrogenase | putA | PRO + FAD -> FADH + GLUGSAL | 1 |
| Pyrroline-5-carboxylate dehydrogenase | putA | GLUGSAL + NAD -> NADH + GLU | 1 |
| Serine deaminase 1 | sdaA | SER -> PYR + NH3 | 1 |
| Serine deaminase 2 | sdaB | SER -> PYR + NH3 | 1 |

TABLE 1-continued

The genes included in the E. coli metabolic genotype along with corresponding enzymes and reactions that comprise the genome specific stoichiometric matrix. The final column indicates the presence/absence of the gene (as the number of copies) in the E. coli genome. Thus the presence of a gene in the E. coli genome indicates that the gene is part of the metabolic genotype. Reactions/Genes not present in the genome are those gathered at state 56 in FIG. 2 and together with the reactions of the genes in the metabolic genotype form the columns of the genome specific stoichiometric matrix.

| Enzyme | Gene | Reaction | E. coli Genome |
|---|---|---|---|
| Trypothanase | tnaA | SER -> PYR + NH3 | 1 |
| D-Serine deaminase | dsdA | DSER -> PYR + NH3 | 1 |
| Threonine dehydrogenase | tdh | THR + NAD -> 2A3O + NADH | 1 |
| Amino ketobutyrate ligase | kbl | 2A3O + COA -> ACCOA + GLY | 1 |
| Threonine dehydratase catabolic | tdcB | THR -> OBUT + NH3 | 1 |
| Threonine deaminase 1 | sdaA | THR -> OBUT + NH3 | 1 |
| Threonine deaminase 2 | sdaB | THR -> OBUT + NH3 | 1 |
| Tryptophanase | tnaA | TRP <-> INDOLE + PYR + NH3 | 1 |
| Amidophosphoribosyl transferase | purF | PRPP + GLN -> PPI + GLU + PRAM | 1 |
| Phosphoribosylamine-glycine ligase | purD | PRAM + ATP + GLY <-> ADP + PI + GAR | 1 |
| Phosphoribosylglycinamide formyltransferase | purN | GAR + FTHF -> THF + FGAR | 1 |
| GAR transformylase T | purT | GAR + FOR + ATP -> ADP + PI + FGAR | 1 |
| Phosphoribosylformylglycinamide synthetase | purL | FGAR + ATP + GLN -> GLU + ADP + PI + FGAM | 1 |
| Phosphoribosylformylglycinamide cyclo-ligase | purM | FGAM + ATP -> ADP + PI + AIR | 1 |
| Phosphoribosylaminoimidazole carboxylase 1 | purK | AIR + CO2 + ATP <-> NCAIR + ADP + PI | 1 |
| Phosphoribosylaminoimidazole carboxylase 2 | purE | NCAIR <-> CAIR | 1 |
| Phosphoribosylaminoimidazole-succinocarboxamide synthetase | purC | CAIR + ATP + ASP <-> ADP + PI + SAICAR | 1 |
| 5'-Phosphoribosyl-4-(N-succinocarboxamide)-5-aminoimidazole lya | purB | SAICAR <-> FUM + AICAR | 1 |
| AICAR transformylase | purH | AICAR + FTHF <-> THF + PRFICA | 1 |
| IMP cyclohydrolase | purH | PRFICA <-> IMP | 1 |
| Adenylosuccinate synthetase | purA | IMP + GTP + ASP -> GDP + PI + ASUC | 1 |
| Adenylosuccinate lyase | purB | ASUC <-> FUM + AMP | 1 |
| IMP dehydrogenase | guaB | IMP + NAD -> NADH + XMP | 1 |
| GMP synthase | guaA | XMP + ATP + GLN -> GLU + AMP + PPI + GMP | 1 |
| GMP reductase | guaC | GMP + NADPH -> NADP + IMY + NH3 | 1 |
| Aspartate-carbamoyltransferase | pyrBI | CAP + ASP -> CAASP + PI | 2 |
| Dihydroorotase | pyrC | CAASP <-> DOROA | 1 |
| Dihydroorotate dehydrogenase | pyrD | DOROA + Q <-> QH2 + OROA | 1 |
| Orotate phosphoribosyl transferase | pyrE | OROA + PRPP <-> PPI + OMP | 1 |
| OMP decarboxylase | pyrF | OMP -> CO2 + UMP | 1 |
| CTP synthetase | pyrG | UTP + GLN + ATP -> GLU + CTP + ADP + PI | 1 |
| Adenylate kinase | adk | ATP + AMP <-> 2 ADP | 1 |
| Adenylate kinase | adk | GTP + AMP <-> ADP + GDP | 1 |
| Adenylate kinase | adk | ITP + AMP <-> ADP + IDP | 1 |
| Adenylate kinase | adk | DAMP + ATP <-> ADP + DADP | 1 |
| Guanylate kinase | gmk | GMP + ATP <-> GDP + ADP | 1 |
| Deoxyguanylate kinase | gmk | DGMP + ATP <-> DGDP + ADP | 1 |
| Nucleoside-diphosphate kinase | ndk | GDP + ATP <-> GTP + ADP | 1 |
| Nucleoside-diphosphate kinase | ndk | UDP + ATP <-> UTP + ADP | 1 |
| Nucleoside-diphosphate kinase | ndk | CDP + ATP <-> CTP + ADP | 1 |
| Nucleoside-diphosphate kinase | ndk | DGDP + ATP <-> DGTP + ADP | 1 |
| Nucleoside-diphosphate kinase | ndk | DUDP + ATP <-> DUTP + ADP | 1 |
| Nucleoside-diphosphate kinase | ndk | DCDP + ATP <-> DCTP + ADP | 1 |
| Nucleoside-diphosphate kinase | ndk | DADP + ATP <-> DATP + ADP | 1 |
| Nucleoside-diphosphate kinase | ndk | DTDP + ATP <-> DTTP + ADP | 1 |
| AMP Nucleosidse | amn | AMP -> AD + R5P | 1 |
| Adenosine deaminase | add | ADN -> INS + NH3 | 1 |
| Deoxyadenosine deaminase | add | DA -> DIN + NH3 | 1 |
| Adenine deaminase | yicP | AD -> NH3 + HYXN | 1 |
| Inosine kinase | gsk | INS + ATP -> IMP + ADP | 1 |
| Guanosine kinase | gsk | GSN + ATP -> GMP + ADP | 1 |
| Adenosine kinase | adk | ADN + ATP -> AMP + ADP | 1 |
| Adenine phosphotyltransferase | apt | AD + PRPP -> PPI + AMP | 1 |
| Xanthine-guanine phosphoribosyltransferase | gpt | XAN + PRPP -> XMP + PPI | 1 |
| Xanthine-guanine phosphoribosyltransferase | gpt | HYXN + PRPP -> PPI + IMP | 1 |
| Hypoxanthine phosphoribosyltransferase | hpt | HYXN + PRPP -> PPI + IMP | 1 |
| Xanthine-guanine pliosphoribosyltransferase | gpt | GN + PRPP -> PPI + GMP | 1 |
| Hypoxanthine phosphoribosyltransferase | hpt | GN + PRPP -> PPI + GMP | 1 |
| Xanthosine phosphorylase | xapA | DIN + PI <-> HYXN + DR1P | 1 |
| Purine nucleotide phosphorylase | deoD | DLN + PI <-> HYXN + DR1P | 1 |
| Xanthosine phosphorylase | xapA | DA + PI <-> AD + DR1P | 1 |
| Purine nucleotide phosphorylase | deoD | DA + PI <-> AD + DR1P | 1 |
| Xanthosine phosphorylase | xapA | DG + PI <-> GN + DR1P | 1 |
| Purine nucleotide phosphorylase | deoD | DG + PI <-> GN + DR1P | 1 |
| Xanthosine phosphorylase | xapA | HYXN + R1P <-> INS + PI | 1 |
| Purine nucleotide phosphorylase | deoD | HYXN + R1P <-> INS + PI | 1 |
| Xanthosine phosphorylase | xapA | AD + R1P <-> PI + ADN | 1 |
| Purine nucleotide phosphorylase | deoD | AD + R1P <-> PI + ADN | 1 |
| Xanthosine phosphorylase | xapA | GN + R1P <-> PI + GSN | 1 |

TABLE 1-continued

The genes included in the *E. coli* metabolic genotype along with corresponding enzymes and reactions that comprise the genome specific stoichiometric matrix. The final column indicates the presence/absence of the gene (as the number of copies) in the *E. coli* genome. Thus the presence of a gene in the *E. coli* genome indicates that the gene is part of the metabolic genotype. Reactions/Genes not present in the genome are those gathered at state 56 in FIG. 2 and together with the reactions of the genes in the metabolic genotype form the columns of the genome specific stoichiometric matrix.

| Enzyme | Gene | Reaction | E. coli Genome |
|---|---|---|---|
| Purine nucleotide phosphorylase | deoD | GN + R1P <-> PI + GSN | 1 |
| Xanthosine phosphorylase | xapA | XAN + R1P <-> PI + XTSN | 1 |
| Purine nucleotide phosphorylase | deoD | XAN + R1P <-> PI + XTSN | 1 |
| Uridine phosphorylase | udp | URI + PI <-> URA + R1P | 1 |
| Thymidine (deoxyuridine) phosphorylase | deoA | DU + PI <-> URA + DR1P | 1 |
| Purine nucleotide phosphorylase | deoD | DU + PI <-> URA + DR1P | 1 |
| Thymidine (deoxyuridine) phosphorylase | deoA | DT + PI <-> THY + DR1P | 1 |
| Cytidylate kinase | cmkA | DCMP + ATP <-> ADP + DCDP | 1 |
| Cytidylate kinase | cmkA | CMP + ATP <-> ADP + CDP | 1 |
| Cytidylate kinase | cmkB | DCMP + ATP <-> ADP + DCDP | 1 |
| Cytidylate kinase | cmkB | CMP + ATP <-> ADP + CDP | 1 |
| Cytidylate kinase | cmkA | UMP + ATP <-> ADP + UDP | 1 |
| Cytidylate kinase | cmkB | UMP + ATP <-> ADP + UDP | 1 |
| dTMP kinase | tmk | DTMP + ATP <-> ADP + DTDP | 1 |
| Uridylate kinase | pyrH | UMP + ATP <-> UDP + ADP | 1 |
| Uridylate kinase | pyrH | DUMP + ATP <-> DUDP + ADP | 1 |
| Thymidine (deoxyuridine) kinase | tdk | DU + ATP -> DUMP + ADP | 1 |
| Uracil phosphoribosyltransferase | upp | URA + PRPP -> UMP + PPI | 1 |
| Cytosine deaminase | codA | CYTS -> URA + NH3 | 1 |
| Uridine kinase | udk | URI + GTP -> GDP + UMP | 1 |
| Cytodine kinase | udk | CYTD + GTP -> GDP + CMP | 1 |
| CMP glycosylase |  | CMP -> CYTS + R5P | 0 |
| Cytidine deaminase | cdd | CYTD -> URI + NH3 | 1 |
| Thymidine (deoxynridine) kinase | tdk | DT + ATP -> ADP + DTMP | 1 |
| dCTP deaminase | dcd | DCTP -> DUTP + NH3 | 1 |
| Cytidine deaminase | cdd | DC -> NH3 + DU | 1 |
| 5'-Nucleotidase | ushA | DUMP -> DU + PI | 1 |
| 5'-Nucleotidase | ushA | DTMP -> DT + PI | 1 |
| 5'-Nucleotidase | ushA | DAMP -> DA + PI | 1 |
| 5'-Nucleotidase | ushA | DGMP -> DG + PI | 1 |
| 5'-Nucleotidase | ushA | DCMP -> DC + PI | 1 |
| 5'-Nucleotidase | ushA | CMP -> CYTD + PI | 1 |
| 5'-Nucleotidase | ushA | AMP -> PI + ADN | 1 |
| 5'-Nucleotidase | ushA | GMP -> PI + GSN | 1 |
| 5'-Nucleotidase | ushA | IMP -> PI + INS | 1 |
| 5'-Nucleotidase | ushA | XMP -> PI + XTSN | 1 |
| 5'-Nucleotidase | ushA | UMP -> PT + URI | 1 |
| Ribonucleoside-diphosphate reductase | nrdAB | ADP + RTHIO -> DADP + OTHIO | 2 |
| Ribonucleoside-diphosphate reductase | nrdAB | GDP + RTHIO -> DGDP + OTHIO | 2 |
| Ribonucleoside-triphosphate reductase | nrdD | ATP + RTHIO -> DATP + OTHIO | 1 |
| Ribonucleoside-triphosphate reductase | nrdD | GTP + RTHIO -> DGTP + OTHIO | 1 |
| Ribonucleoside-diphosphate reductase | nrdAB | CDP + RTHIO -> DCDP + OTHIO | 2 |
| Ribonucleoside-diphosphate reductase II | nrdEF | CDP + RTHIO -> DCDP + OTHIO | 2 |
| Ribonucleoside-diphosphate reductase | nrdAB | UDP + RTHIO -> DUDP + OTHIO | 2 |
| Ribonucleoside-triphosphate reductase | nrdD | CTP + RTHIO -> DCTP + OTHIO | 1 |
| Ribonucleoside-triphosphate reductase | nrdD | UTP + RTHIO -> OTHIO + DUTP | 1 |
| dUTP pyrophosphatase | dut | DUTP -> PPI + DUMP | 1 |
| Thymidilate synthetase | thyA | DUMP + METTHF -> DHF + DTMP | 1 |
| Nucleoside triphosphatase | mutT | GTP -> GSN + 3 PI | 1 |
| Nucleoside triphosphatase | mutT | DGTP -> DG + 3 PI | 1 |
| Deoxyguanosinetriphosphate triphophohydrolase | dgt | DGTP -> DG + 3 PI | 1 |
| Deoxyguanosinetriphosphate triphophohydrolase | dgt | GTP -> GSN + 3 PI | 1 |
| Glycine cleavage system (Multi-component system) | gcvHTP, IpdA | GLY + THF + NAD -> METTHF + NADH + CO2 + NH3 | 4 |
| Formyl tetrahydrofolate deformylase | purU | FTHF -> FOR + THF | 1 |
| Methylene tetrahydrofolate reductase | metF | METTHF + NADH -> NAD + MTHF | 1 |
| Methylene THF dehydrogenase | folD | METTHF + NADP <-> METHF + NADPH | 1 |
| Methenyl tetrahydrofolate cyclehydrolase | folD | METHE <-> FTHF | 1 |
| Acetyl-CoA carboxyltransferase | accABD | ACCOA + ATP + CO2 <-> MALCOA + ADP + PI | 3 |
| Malonyl-CoA-ACP transacylase | fabD | MALCOA + ACP <-> MALACP + COA | 1 |
| Malonyl-ACP decarboxylase | fadB | MALACP -> ACACP + CO2 | 1 |
| Acetyl-CoA-ACP transacylase | fabH | ACACP + COA <-> ACCOA + ACP | 1 |
| Acyltransferase | pis | GL3P + 0.035 C140ACP + 0.102 C141ACP + 0.717 C160AC | 0 |
| CDP-Diacylglycerol synthetase | cdsA | PA + CTP <-> CDPDG + PPI | 1 |
| CDP-Diacylglycerol pyrophosphatase | cdh | CDPDG -> CMP + PA | 1 |
| Phosphatidylserine synthase | pssA | CDPDG + SER <-> CMP + PS | 1 |
| Phosphatidylserine decarboxylase | psd | PS -> PE + CO2 | 1 |
| Phosphatidylglycerol phosphate synthase | pgsA | CDPDG + GL3P <-> CMP + PGP | 1 |
| Phosphatidylglycerol phosphate phosphatase A | pgpA | PGP -> PI + PG | 0 |
| Phosphatidylglycerol phosphate phosphatase B | pgpB | PGP -> PI + PG | 1 |
| Cardiolipin synthase | cls | 2 PG <-> CL + GL | 1 |
| Acetyl-CoA C-acetyltransferase | atoB | 2 ACCOA <-> COA + AACCOA | 1 |

TABLE 1-continued

The genes included in the E. coli metabolic genotype along with corresponding enzymes and reactions that comprise the genome specific stoichiometric matrix. The final column indicates the presence/absence of the gene (as the number of copies) in the E. coli genome. Thus the presence of a gene in the E. coli genome indicates that the gene is part of the metabolic genotype. Reactions/Genes not present in the genome are those gathered at state 56 in FIG. 2 and together with the reactions of the genes in the metabolic genotype form the columns of the genome specific stoichiometric matrix.

| Enzyme | Gene | Reaction | E. coli Genome |
|---|---|---|---|
| Isoprenyl-pyrophosphate synthesis pathway | | T3P1 + PYR + 2 NADPH + ATP- > IPPP + ADP + 2 NADP + | 0 |
| Isoprenyl pyrophosphate isomerase | | IPPP -> DMPP | 0 |
| Farnesyl pyrophosphate synthetase | ispA | DMPP + IPPP -> GPP + PPI | 1 |
| Geranyltranstransferase | ispA | GPP + IPPP -> FPP + PPI | 1 |
| Octoprenyl pyrophosphate synthase (5 reactions) | ispB | 5 IPPP + FPP -> OPP + 5 PPI | 1 |
| Undecaprenyl pyrophosphate synthase (8 reactions) | | 8 IPPP + FPP -> UDPP + 8 PPI | 0 |
| Chorismate pyruvate-lyase | ubiC | CHOR -> 4HBZ + PYR | 1 |
| Hydroxybenzoate octaprenyltransferase | ubiA | 4HBZ + OPP -> O4HBZ + PPI | 1 |
| Octaprenyl-hydroxybeuzoate decarboxylase | ubiD, ubiX | O4HBZ -> CO2 + 2OPPP | 1 |
| 2-Octaprenylphenol hydroxylase | ubiB | 2OPPP + O2 -> 2O6H | 1 |
| Methylation reaction | | 2O6H + SAM -> 2OPMP + SAH | 0 |
| 2-Octaprenyl-6-methoxyphenol hydroxylase | ubiH | 2OPMP + O2 -> 2OPMB | 1 |
| 2-Octaprenyl-6-methoxy-1,4-benzoquinone methylase | ubiE | 2OPMB + SAM -> 2OPMMB + SAH | 0 |
| 2-Octaprenyl-3-methyl-6-methoxy-1,4-benzoquinone hydroxylase | ubiF | 2OPMMB + O2 -> 2OMHMB | 0 |
| 3-Dimethylubiquinone 3-methyltransferase | ubiG | 2OMHMB + SAM -> QH2 + SAH | 1 |
| Isochorismate synthase 1 | menF | CHOR -> ICHOR | 1 |
| α-Ketoglutarate decarboxylase | menD | AKG + TPP -> SSALTPP + CO2 | 1 |
| SHCHC synthase | menD | ICHOR + SSALTPP -> PYR + TPP + SHCHC | 1 |
| O-Succinylbenzoate-CoA synthase | menC | SHCHC -> OSB | 1 |
| O-Succinylbenzoic acid-CoA ligase | menE | OSB + ATP + COA -> OSBCOA + AMP + PPI | 1 |
| Naphthoate synthase | menB | OSBCOA -> DHNA + COA | 1 |
| 1,4-Dihydroxy-2-naphthoate octaprenyltransferase | menA | DHNA + OPP -> DMK + PPI + CO2 | 1 |
| S-Adenosylmethionine-2-DMK methyltransferase | menG | DMK + SAM -> MK + SAH | 1 |
| Isochorismate synthase 2 | entC | CHOR -> ICHOR | 1 |
| Isochorismatase | entB | ICHOR <-> 23DHDHB + PYR | 1 |
| 2,3-Dihydo-2,3-dihydroxybenzoate dehydrogenase | entA | 23DHDHB + NAD <-> 23DHB + NADH | 1 |
| ATP-dependent activation of 2,3-dihydroxybenzoate | entE | 23DHB + ATP <-> 23DHBA + PPI | 1 |
| ATP-dependent serine activating enzyme | entF | SER + ATP <-> SERA + PPI | 1 |
| Enterochelin synthetase | entD | 3 SERA + 3 23DHBA -> ENTER + 6 AMP | 1 |
| GTP cyclohydrolase II | ribA | GTP -> D6RP5P + FOR + PPI | 1 |
| Pryimidine deaminase | ribD | D6RP5P -> A6RP5P + NH3 | 1 |
| Pyrimidine reductase | ribD | A6RP5P + NADPH -> A6RP5P2 + NADP | 1 |
| Pyrimidine phosphatase | | A6RP5P2 -> A6RP + PI | 0 |
| 3,4 Dihydroxy-2-butanone-4-phosphate synthase | ribB | RL5P -> DB4P + FOR | 1 |
| 6,7-Dimethyl-8-ribityllumazine synthase | ribE | DB4P + A6RP -> D8RL + PI | 1 |
| Riboflavin synthase | ribH | 2 D8RL -> RIBFLV + A6RP | 1 |
| Riboflavin kinase | ribF | RIBFLV + ATP -> FMN + ADP | 1 |
| FAD synthetase | ribF | FMN + ATP -> FAD + PPI | 1 |
| GTP cyclohydrolase I | folE | GTP -> FOR + AHTD | 1 |
| Dihydroneopterin triphosphate pyrophosphorylase | ntpA | AHTD -> PPI + DHPP | 1 |
| Nucleoside triphosphatase | mutT | AHTD -> DHP + 3 PI | 1 |
| Dihydroneopterin monophosphate dephosphorylase | | DHPP -> DHP + PI | 0 |
| Dihydroneopterin aldolase | folB | DHP -> AHHMP + GLAL | 1 |
| 6-Hydroxymethyl-7,8-dihydropterin pyrophosphokinase | folK | AHHMP + ATP -> AMP + AHHMD | 1 |
| Aminodeoxychorismate synthase | pabAB | CHOR + GLN -> ADCHOR + GLU | 2 |
| Aminodeoxychorismate lyase | pabC | ADCHOR -> PYR + PABA | 1 |
| Dihydropteroate synthase | folP | PABA + AHHMD -> PPI + DHPT | 1 |
| Dihydrofolate synthetase | folC | DHPT + ATP + GLU -> ADP + PI + DHF | 1 |
| Dihydrofolate reductase | folA | DHF + NADPH -> NADP + THF | 1 |
| Ketopentoate hydroxymethyl transferase | panB | OIVAL + METTHF -> AKP + THF | 1 |
| Ketopantoate reductase | panE | AKP + NADPH -> NADP + PANT | 0 |
| Acetohyoxyacid isomeroreductase | ilvC | AKP + NADPH -> NADP + PANT | 1 |
| Aspartate decarboxylase | panD | ASP -> CO2 + bALA | 1 |
| Pantoate-β-alanine ligase | panC | PANT + bALA + ATP -> AMP + PPI + PNTO | 1 |
| Pantothenate kinase | coaA | PNTO + ATP -> ADP + 4PPNTO | 1 |
| Phosphopantothenate-cysteine ligase | | 4PPNTO + CTP + CYS -> CMP + PPI + 4PPNCYS | 0 |
| Phosphopantothenate-cysteine decarboxylase | | 4PPNCYS -> CO2 + 4PPNTE | 0 |
| Phospho-pantetheine adenylyltransferase | | 4PPNTE + ATP -> PPI + DPCOA | 0 |
| DephosphoCoA kinase | | DPCOA + ATP -> ADP + COA | 0 |
| ACP Synthase | acpS | COA -> PAP + ACP | 1 |
| Aspartate oxidase | nadB | ASP + FAD -> FADH + ISUCC | 1 |
| Quinolate synthase | nadA | ISUCC + T3P2 -> PI + QA | 1 |
| Quinolate phosphoribosyl transferase | nadC | QA + PRPP -> NAMN + CO2 + PPI | 1 |
| NAMN adenylyl transferase | nadD | NAMN + ATP -> PPI + NAAD | 0 |
| NAMN adenylyl transferase | nadD | NMN + ATP -> NAD + PPI | 0 |
| Deaniido-NAD ammonia ligase | nadE | NAAD + ATP + NH3 -> NAD + AMP + PPI | 1 |
| NAD kinase | nadFG | NAD + ATP -> NADP + ADP | 0 |
| NADP phosphatase | | NADP -> NAD + PI | 0 |
| DNA ligase | lig | NAD -> NMN + AMP | 1 |
| NMN amidohydrolase | pncC | NMN -> NAMN + NH3 | 0 |

TABLE 1-continued

The genes included in the E. coli metabolic genotype along with corresponding enzymes and reactions that comprise the genome specific stoichiometric matrix. The final column indicates the presence/absence of the gene (as the number of copies) in the E. coli genome. Thus the presence of a gene in the E. coli genome indicates that the gene is part of the metabolic genotype. Reactions/Genes not present in the genome are those gathered at state 56 in FIG. 2 and together with the reactions of the genes in the metabolic genotype form the columns of the genome specific stoichiometric matrix.

| Enzyme | Gene | Reaction | E. coli Genome |
|---|---|---|---|
| NMN glycohydrolase (cytoplasmic) | | NMN -> R5P + NAm | 0 |
| NAm amidohydrolase | pncA | NAm -> NAC + NH3 | 0 |
| NAPRTase | pncB | NAC + PRPP + ATP -> NAMN + PPI + PI + ADP | 1 |
| NMD pyrophosphatase | pnuE | NADxt -> NMNxt + AMPxt | 0 |
| NMN permease | pnuC | NMNxt -> NMN | 1 |
| NMN glycohydrolase (membrane bound) | | NMNxt -> R5P + NAm | 0 |
| Nicotinic acid uptake | | NACxt -> NAC | 0 |
| GSA synthetase | hemM | GLU + ATP -> GTRNA + AMP + PPI | 1 |
| Glutamyl-tRNA synthetase | gltX | GLU + ATP -> GTRNA + AMP + PPI | 1 |
| Glutamyl-tRNA reductase | hemA | GTRNA + NM)PI1 -> GSA + NADP | 1 |
| Glutamate-1-semialdehyde aminotransferase | hemL | GSA -> ALAV | 1 |
| Porphobilinogen synthase | hemB | 8 ALAV -> 4PBG | 1 |
| Hydroxymethylbilane synthase | hemC | 4PBG -> HMB + 4 NH3 | 1 |
| Uroporphyrinogen III synthase | hemD | HMB -> UPRG | 1 |
| Uroporphyrin-III C-methyltransferase 1 | hemX | SAM + UPRG -> SAH + PC2 | 1 |
| Uroporphyrin-III C-methyltransferase 2 | cysG | SAM + UPRG-> SAH + PC2 | 1 |
| 1,3-Dimethyluroporphyrinogen III dehydrogenase | cysG | PC2 + NAD -> NADH + SHCL | 1 |
| Siroheme ferrochelatase | cysG | SHCL -> SHEME | 1 |
| Uroporphyrinogen decarboxylase | hemE | UPRG -> 4 CO2 + CPP | 1 |
| Coproporphyrinogen oxidase, aerobic | hemF | O2 + CPP -> 2 CO2 + PPHG | 2 |
| Protoporphyrinogen oxidase | hemG | O2 + PPHG -> PPIX | 2 |
| Ferrochelatase | hemH | PPIX -> PTH | 1 |
| Heme O synthase | cyoE | PTH + FPP -> HO + PPI | 1 |
| 8-Amino-7-oxononanoate synthase | bioF | ALA + CHCOA <-> CO2 + COA + AONA | 1 |
| Adenosylmethionine-8-amino-7-oxononanoate aminotransferase | bioA | SAM + AONA <-> SAMOB + DANNA | 1 |
| Dethiobiotin synthase | bioD | CO2 + DANNA + ATP <-> DTB + PI + ADP | 1 |
| Biotin synthase | bioB | DTB + CYS <-> BT | 1 |
| Glutamate-cysteine ligase | gshA | CYS + GLU + ATP -> GC + PI + ADP | 1 |
| Glutathione synthase | gshB | GLY + GC + ATP -> RGT + PI + ADP | 1 |
| Glutathione reductase | gor | NADPH + OGT <-> NADP + RGT | 1 |
| thiC protein | thiC | AIR-> AHM | 1 |
| HMP kinase | thiN | AHM + ATP -> AHMP + ADP | 0 |
| HMP-phosphate kinase | thiD | AHMP + ATP -> AHMPP + ADP | 1 |
| Hypothetical | | T3P1 + PYR -> DTP | 0 |
| thiG protein | thiG | DTP + TYR + CYS -> THZ + HBA + CO2 | 1 |
| thiE protein | thiE | DTP + TYR + CYS -> THZ + HBA + CO2 | 1 |
| thiF protein | thiF | DTP + TYR + CYS -> THZ + HBA + CO2 | 1 |
| thiH protein | thiH | DTP + TYR + CYS -> THZ + HBA + CO2 | 1 |
| THZ kinase | thiM | THZ + ATP -> THZP + ADP | 0 |
| Thiamin phosphate synthase | thiB | THZP + AHMPP -> THMP + PPI | 0 |
| Thiamin kinase | thiK | THMP + ADP <-> THIAMIN + ATP | 0 |
| Thiamin phosphate kinase | thiL | THMP + ATP <-> TPP + ADP | 0 |
| Erythrose 4-phosphate dehydrogenase | epd | E4P + NAD <-> ER4P + NADH | 1 |
| Erythronate-4-phosphate dehydrogenase | pdxB | ER4P + NAD <-> OHB + NADH | 1 |
| Hypothetical transaminase/phosphoserine transaminase | serC | OHB + GLU <-> PHT + AKG | 1 |
| Pyridoxal-phosphate biosynthetic proteins pdxJ-pdxA | pdxAJ | PHT + DX5P -> P5P + CO2 | 2 |
| Pyridoxine 5'-phosphate oxidase | pdxH | P5P + O2 <-> PL5P + H2O2 | 1 |
| Threonine synthase | thrC | PHT -> 4HLT + PI | 1 |
| Hypothetical Enzyme | | 4HLT -> PYRDX | 0 |
| Pyridoxine kinase | pdxK | PYRDX + ATP -> P5P + ADP | 1 |
| Hypothetical Enzyme | | P5P -> PYRDX + PI | 0 |
| Hypothetical Enzyme | | PL5P -> PL + PI | 0 |
| Pyridoxine kinase | pdxK | PL + ATP -> PL5P + ADP | 1 |
| Pyridoxine 5'-phosphate oxidase | pdxH | PYRDX + O2 <-> PL + H2O2 | 1 |
| Pyridoxine 5'-phosphate oxidase | pdxH | PL + O2 + NH3 <-> PDLA + H2O2 | 1 |
| Pyridoxine kinase | pdxK | PDLA + ATP -> PDLA5P + ADP | 1 |
| Hypothetical Enzyme | | PDLA5P -> PDLA + PI | 0 |
| Pyridoxine 5'-phosphate oxidase | pdxH | PDLA5P + O2 -> PL5P + H2O2 + NH3 | 1 |
| Serine hydroxymethyltransferase (serine methylase) | glyA | PL5P + GLU -> PDLA5P + AKG | 1 |
| Serine hydroxymethyltransferase (serile methylase) | glyA | PL5P + ALA -> PDLA5P + PYR | 1 |
| Glutamine fmctose-6-phosphate Transaminase | glmS | F6P + GLN -> GLU + GA6P | 1 |
| Phosphoglucosamine mutase | glmM | GA6P <-> GA1P | 0 |
| N-Acetylglucosamine-1-phosphate-uridyltransferase | glmU | UTP + GA1P + ACCOA -> UDPNAG + PPI + COA | 1 |
| UDP-N-acetylglucosamine acyltransferase | lpxA | C140ACP + UDPNAG -> ACP + UDPG2AA | 1 |
| UDP-3-O-acyl-N-acetylglucosamine deacetylase | lpxC | UDPG2AA -> UDPG2A + AC | 1 |
| UDP-3-O-(3-hydroxymyristoyl)glucosamine-acyltransferase | lpxD | UDPG2A + C140ACP -> ACP + UDPG23A | 1 |
| UDP-sugar hydrolase | ushA | UDPG23A -> UMP + LIPX | 1 |
| Lipid A disaccharide synthase | lpxB | LIPX + UDPG23A -> UDP + DISAC1P | 1 |
| Tetraacyldisaccharide 4' kinase | | DISAC1P + ATP -> ADP + LIPIV | 0 |

TABLE 1-continued

The genes included in the E. coli metabolic genotype along with corresponding enzymes and reactions that comprise the genome specific stoichiometric matrix. The final column indicates the presence/absence of the gene (as the number of copies) in the E. coli genome. Thus the presence of a gene in the E. coli genome indicates that the gene is part of the metabolic genotype. Reactions/Genes not present in the genome are those gathered at state 56 in FIG. 2 and together with the reactions of the genes in the metabolic genotype form the columns of the genome specific stoichiometric matrix.

| Enzyme | Gene | Reaction | E. coli Genome |
|---|---|---|---|
| 3-Deoxy-D-manno-octulosonic-acid transferase (KDO transferase) | kdtA | LIPIV + CMPKDO -> KDOLIPIV + CMP | 1 |
| 3-Deoxy-D-manno-octulosonic-acid transferase (KDO transferase) | kdtA | KDOLIPIV + CMPKDO -> K2LIPIV + CMP | 1 |
| Endotoxin synthase | htrB, msbB | K2LIPIV + C140ACP + C120ACP -> LIPA + 2 ACP | 2 |
| 3-Deoxy-D-manno-octulosonic-acid 8-phosphate synthase | kdsA | PEP + A5P -> KDOP + PI | 1 |
| 3-Deoxy-D-manno-octulosonic-acid 8-phosphate phosphatase | | KDOP -> KDO + PI | 0 |
| CMP-2-keto-3-deoxyoctonate synthesis | kdsB | KDO + CTP -> PPI + CMPKDO | 1 |
| ADP-L-glycero-D-mannoheptose-6-epimerase | lpcA, rfaED | S7P + ATP -> ADPHEP + PPI | 1 |
| UDP glucose-1-phosphate uridylyltransferase | galU, galF | G1P + UTP -> PPI + UDPG | 2 |
| Ethanolamine phosphotransferase | | PE + CMP<-> CDPETN + DGR | 0 |
| Phosphatidate phosphatase | | PA -> PI + DGR | 0 |
| Diacylglycerol kinase | dgkA | DGR + ATP-> ADP + PA | 1 |
| LPS Synthesis - truncated version of LPS (ref neid) | rfaLJIGFC | LIPA + 3 ADPHEP + 2 UDPG + 2 CDPETN + 3 CMPKDO -> | 6 |
| UDP-N-acetylglucosamine-enolpyruvate transferase | murA | UDPNAG + PEP -> UDPNAGEP + PI | 1 |
| UDP-N-acetylglucosamine-enolpyruvate dehydrogenase | murB | UDPNAGEP + NADPH -> UDPNAM + NADP | 1 |
| UDP-N-acetylmuramate-alanine ligase | murC | UDPNAM + ALA + ATP -> ADP + PI + UDPNAMA | 1 |
| UDP-N-acetylmuramoylalanine-D-glutamate ligase | murD | UDPNAMA + DGLU + ATP -> UDPNAMAG + ADP + PI | 1 |
| UDP-N-acetylmuramoylalanyl-D-glutamate 2,6-diamino-pimelate lig | murE | UDPNAMAG + ATP + MDAP -> UNAGD + ADP + PI | 1 |
| D-Alanine-D-alanine adding enzyme | murF | UNAGD + ATP + AA -> UNAGDA + ADP + PI | 1 |
| Glutamate racemase | murI | GLU <-> DGLU | 1 |
| D-ala:D-ala ligases | ddlAB | 2 DALA <-> AA | 2 |
| Phospho-N-acetylmuramoylpentapeptide transferase | mraY | UNAGDA -> UMP + PI + UNPTDO | 1 |
| N-Acetylglucosaminyl transferase | murG | UNPTDO + UDPNAG -> UDP + PEPTIDO | 1 |
| Arabinose (low affinity) | araE | ARABxt + HEXT <-> ARAB | 1 |
| Arabinose (high affinity) | araFGH | ARABxt + ATP -> ARAB + ADP + PI | 3 |
| Dihydroxyacetone | | DHAxt + PEP -> T3P2 + PYR | 0 |
| Fructose | fruABF | FRUxt + PEP -> F1P + PYR | 2 |
| Fucose | fucP | FUCxt + HEXT <-> FUC | 1 |
| Galacitol | gatABC | GLTLxt + PEP -> GLTL1P + PYR | 3 |
| Galactose (low affinity) | galP | GLACxt + HEXT -> GLAC | 1 |
| Galactose (low affinity) | galP | GLCxt + HEXT -> GLC | 1 |
| Galactose (high affinity) | mglABC | GLACxt + ATP -> GLAC + ADP + PI | 3 |
| Glucitol | srlA1A2B | GLTxt + PEP -> GLT6P + PYR | 3 |
| Gluconate | gntST | GLCNxt + ATP -> GLCN + ADP + PT | 1 |
| Glucose | ptsG, crr | GLCxt + PEP -> G6P + PYR | 2 |
| Glycerol | glpF | GLxt <-> GL | 1 |
| Lactose | lacY | LCTSxt + NEXT <-> LCTS | 1 |
| Maltose | malX, crr, malE | MLTxt + PEP -> MLT6P + PYR | 7 |
| Mannitol | mtlA, cmtAB | MNTxt + PEP -> MNT6P + PYR | 3 |
| Mannose | manATZ, ptsPA | MANxt + PEP -> MAN1P + PYR | 6 |
| Melibiose | melB | MELIxt + HEXT -> MELI | 1 |
| N-Acetylglucosamine | nagE, ptsN | NAG + PEP -> NAGP + PYR | 2 |
| Rhamnose | rhaT | RMNxt + ATP -> RMN + ADP + PI | 1 |
| Ribose | rbsABCD, xylH | RIBxt + ATP -> RIB + ADP + PI | 5 |
| Sucrose | scr | SUCxt + PEP -> SUC6P + PYR | 0 |
| Trehalose | treAB | TRExt + PEP -> TRE6P + PYR | 2 |
| Xylose (low affinity) | xylE | XYLxt + NEXT -> XYL | 1 |
| Xylose (high affinity) | xylFG, rbsB | XYLxt + ATP -> XYL + ADP + PI | 3 |
| Alanine | cycA | ALAxt + ATP -> ALA + ADP + PI | 1 |
| Arginine | artPMQJI, arg | ARGxt + ATP -> ARG + ADP + PI | 9 |
| Asparagine (low Affinity) | | ASNxt + HEXT <-> ASN | 0 |
| Asparagine (high Affinity) | | ASNxt + ATP -> ASN + ADP + PI | 0 |
| Aspartate | gltP | ASPxt + HEXT -> ASP | 1 |
| Aspartate | gltJKL | ASPxt + ATP -> ASP + ADP + PI | 3 |
| Branched chain amino acid transport | brnQ | BCAAxt + HEXT <-> BCAA | 1 |
| Cysteine | not identified | CYSxt + ATP -> CYS + ADP + PI | 0 |
| D-Alanine | cycA | DALAxt + ATP -> DALA + ADP + PI | 1 |
| D-Alanine glycine permease | cycA | DALAxt + HEXT <-> DALA | 1 |
| D-Alanine glycine permease | cycA | DSERxt + HEXT <-> DSER | 1 |
| D-Alanine glycine permease | cycA | GLYxt + HEXT <-> GLY | 1 |
| Diaminopimelic acid | | MDAPxt + ATP -> MDAP + ADP + PI | 0 |
| γ-Aminobutyrate transport | gabP | GABAxt + ATP -> GABA + ADP + PI | 1 |
| Glutamate | gltP | GLUxt + HEXT <-> GLU | 1 |
| Glutamate | gltS | GLUxt + HEXT <-> GLU | 1 |
| Glutamate | gltJKL | GLUxt + ATP -> GLU + ADP + PI | 3 |
| Glutamine | glnHPQ | GLNxt + ATP -> GLN + ADP + PI | 3 |
| Glycine | cycA, proVWX | GLYxt + ATP -> GLY + ADP + PI | 4 |

TABLE 1-continued

The genes included in the *E. coli* metabolic genotype along with corresponding enzymes and reactions that comprise the genome specific stoichiometric matrix. The final column indicates the presence/absence of the gene (as the number of copies) in the *E. coli* genome. Thus the presence of a gene in the *E. coli* genome indicates that the gene is part of the metabolic genotype. Reactions/Genes not present in the genome are those gathered at state 56 in FIG. 2 and together with the reactions of the genes in the metabolic genotype form the columns of the genome specific stoichiometric matrix.

| Enzyme | Gene | Reaction | E. coli Genome |
|---|---|---|---|
| Histidine | hisJMPQ | HISxt + ATP -> HIS + ADP + PI | 4 |
| Isoleucine | livJ | ILExt + ATP -> ILE + ADP + PI | 1 |
| Leucine | livHKM/livFGJ | LEUxt + ATP -> LEU + ADP + PI | 6 |
| Lysine | lysP | LYSxt + HEXT <-> LYS | 1 |
| Lysine | argT, hisMPQ | LYSxt + ATP -> LYS + ADP + PI | 4 |
| Lysine/Cadaverine | cadB | LYSxt + ATP -> LYS + ADP + PI | 1 |
| Methionine | metD | METxt + ATP -> MET + ADP + PI | 0 |
| Ornithine | argT, hisMPQ | ORNxt + ATP -> ORN + ADP + PI | 4 |
| Phenlyalanine | aroP/mtr/pheP | PHExt + HEXT <-> PHE | 3 |
| Proline | putP, proPWX | PROxt + HEXT <-> PRO | 4 |
| Proline | cycA, proVW | PROxt + ATP -> PRO + ADP + PI | 4 |
| Putrescine | potEFHIG | PTRCxt + ATP -> PTRC + ADP + PI | 5 |
| Serine | sdaC | SERxt + HEXT <-> SER | 1 |
| Serine | cycA | SERxt + ATP -> SER + ADP + PI | 1 |
| Spermidine & putrescine | potABCD | SPMDxt + ATP -> SPMD + ADP + PI | 4 |
| Spermidine & putrescine | potABCD | PTRCxt + ATP -> PTRC + ADP + PI | 4 |
| Threonine | livJ | THRxt + ATP -> THR + ADP + PI | 1 |
| Threonine | tdcC | THRxt + HEXT <-> THR | 1 |
| Tryptophan | tnaB | TRPxt + HEXT <-> TRP | 1 |
| Tyrosine | tyrP | TYRxt + HEXT <-> TYR | 1 |
| Valine | livJ | VALxt + ATP -> VAL + ADP + PI | 1 |
| Dipeptide | dppABCDF | DIPEPxt + ATP -> DIPEP + ADP + PI | 5 |
| Oligopeptide | oppABCDF | OPEPxt + ATP -> OPEP + ADP + PI | 5 |
| Peptide | sapABD | PEPTxt + ATP -> PEPT + ADP + PI | 3 |
| Uracil | uraA | URAxt + HEXT -> URA | 1 |
| Nicotinamide mononucleotide transporter | pnuC | NMNxt + HEXT -> + NMN | 1 |
| Cytosine | codB | CYTSxt + HEXT -> CYTS | 1 |
| Adenine | purB | ADxt + HEXT -> AD | 1 |
| Guanine | gpt, hpt | GNxt <-> GN | 2 |
| Hypoxanthine | gpt, hpt | HYXNxt <-> HYXN | 2 |
| Xanthosine | xapB | XTSNxt <-> XTSN | 1 |
| Xanthine | gpt | XANxt <-> XAN | 1 |
| G-system | nupG | ADNxt + NEXT -> ADN | 1 |
| G-system | nupG | GSNxt + NEXT -> GSN | 1 |
| G-system | nupG | URIxt + NEXT -> URI | 1 |
| G-system | nupG | CYTDxt + HEXT -> CYTD | 1 |
| G-system (transports all nucleosides) | nupG | INSxt + HEXT -> INS | 1 |
| G-system | nupG | XTSNxt + HEXT -> XTSN | 1 |
| G-system | nupG | DTxt + HEXT -> DT | 1 |
| G-system | nupG | DINxt + HEXT -> DIN | 1 |
| G-system | nupG | DGxt + HEXT -> DG | 1 |
| G-system | nupG | DAxt + HEXT -> DA | 1 |
| G-system | nupG | DCxt + HEXT -> DC | 1 |
| G-system | nupG | DUxt + HEXT -> DU | 1 |
| C-system | nupC | ADNxt + HEXT -> ADN | 1 |
| C-system | nupC | URIxt + HEXT -> UIRI | 1 |
| C-system | nupC | CYTDxt + HEXT -> CYTD | 1 |
| C-system | nupC | DTxt + HEXT -> DT | 1 |
| C-system | nupC | DAxt + HEXT -> DA | 1 |
| C-system | nupC | DCxt + HEXT -> DC | 1 |
| C-system | nupC | DUxt + HEXT -> DU | 1 |
| Nucleosides and deoxynucleoside | tsx | ADNxt + HEXT -> ADN | 1 |
| Nucleosides and deoxynucleoside | tsx | GSNxt + HEXT -> GSN | 1 |
| Nucleosides and deoxynucleoside | tsx | URIxt + HEXT -> URI | 1 |
| Nucleosides and deoxynucleoside | tsx | CYTDxt + HEXT -> CYTD | 1 |
| Nucleosides and deoxynucleoside | tsx | INSxt + HEXT -> INS | 1 |
| Nucleosides and deoxynucleoside | tsx | XTSNxt + HEXT -> XTSN | 1 |
| Nucleosides and deoxynucleoside | tsx | DTxt + HEXT -> DT | 1 |
| Nucleosides and deoxynucleoside | tsx | DINxt + HEXT -> DIN | 1 |
| Nucleosides and deoxynucleoside | tsx | DGxt + HEXT -> DG | 1 |
| Nucleosides and deoxynucleoside | tsx | DAxt + HEXT -> DA | 1 |
| Nucleosides and deoxynucleoside | tsx | DCxt + HEXT -> DC | 1 |
| Nucleosides and deoxynucleoside | tsx | DUxt + HEXT -> DU | 1 |
| Acetate transport | | ACxt + HEXT <-> AC | 0 |
| Lactate transport | | LACxt + HEXT <-> LAC | 0 |
| L-Lactate | lldP | LLACxt + HEXT <-> LLAC | 1 |
| Formate transport | focA | FORxt <-> FOR | 1 |
| Ethanol transport | | ETHxt + HEXT <-> ETH | 0 |
| Succinate transport | dcuAB | SUCCxt + HEXT <-> SUCC | 2 |
| Pyruvate transport | | PYRxt + HEXT <-> PYR | 0 |
| Ammonia transport | amtB | NH3xt + HEXT <-> NH3 | 1 |

TABLE 1-continued

The genes included in the E. coli metabolic genotype along with corresponding enzymes and reactions that comprise the genome specific stoichiometric matrix. The final column indicates the presence/absence of the gene (as the number of copies) in the E. coli genome. Thus the presence of a gene in the E. coli genome indicates that the gene is part of the metabolic genotype. Reactions/Genes not present in the genome are those gathered at state 56 in FIG. 2 and together with the reactions of the genes in the metabolic genotype form the columns of the genome specific stoichiometric matrix.

| Enzyme | Gene | Reaction | E. coli Genome |
|---|---|---|---|
| Potassium transport | kdpABC | Kxt + ATP -> K + ADP + PI | 3 |
| Potassium transport | trkAEHG | Kxt + HEXT K-> K | 3 |
| Sulfate transport | cysPTUWAZ, s | SLFxt + ATP -> SLF + ADP + PI | 7 |
| Phosphate transport | pstABCS | PIxt + ATP -> ADP + 2 PI | 4 |
| Phosphate transport | pitAB | PIxt + HEXT <-> PI | 2 |
| Glycerol-3-phosphate | glpT, ugpABCE | GL3Pxt + PI -> GL3P | 5 |
| Dicarboxylates | dcuAB, dctA | SUCCxt + HEXT <-> SUCC | 3 |
| Dicarboxylates | dcuAB, dctA | FUMxt + HEXT <-> FUM | 3 |
| Dicarboxylates | dcuAB, dctA | MALxt + HEXT <-> MAL | 3 |
| Dicarboxylates | dcuAB, dctA | ASPxt + HEXT <-> ASP | 3 |
| Fatty acid transport | fadL | C140xt -> C140 | 1 |
| Fatty acid transport | fadL | C160xt -> C160 | 1 |
| Fatty acid transport | fadL | C180xt -> C180 | 1 |
| α-Ketoglutarate | kgtP | AKGxt + HEXT <-> AKG | 1 |
| Na/H antiporter | nhaABC | NAxt + <-> NA + HEXT | 2 |
| Na/H antiporter | chaABC | NAxt + <-> NA + HEXT | 3 |
| Pantothenate | panF | PNTOxt + HEXT <-> PNTO | 1 |
| Sialic acid permease | nanT | SLAxt + ATP -> SLA + ADP + PI | 1 |
| Oxygen transport | | O2xt <-> O2 | 0 |
| Carbon dioxide transport | | CO2xt <-> CO2 | 0 |
| Urea transport | | UREAxt + 2 HEXT <-> UREA | 0 |
| AU drain flux for constant maintanence requirements | | ATP -> ADP + PI | 0 |
| Glyceraldehyde transport | gufP | GLALxt <-> GLAL | 0 |
| Acetaldehyde transport | | ACALxt <-> ACAL | 0 |

TABLE 2

Comparison of the predicted mutant growth characteristics from the gene deletion study to published experimental results with single and double mutants.

| Gene | Glucose (in vivo/in silico) | Glycerol (in vivo/in silico) | Succinate (in vivo/in silico) | Acetate (in vivo/in silico) |
|---|---|---|---|---|
| aceEF | −/+ | | | |
| aceA | | | | −/− |
| aceB | | | | −/− |
| ackA | | | | +/+ |
| acs | | | | +/+ |
| acn | −/− | −/− | −/− | −/− |
| cyd | +/+ | | | |
| cyo | +/+ | | | |
| eno | −/+ | −/+ | −/− | −/− |
| fba | −/+ | | | |
| fbp | +/+ | −/− | −/− | −/− |
| gap | −/− | −/− | −/− | −/− |
| gltA | −/− | −/− | −/− | −/− |
| gnd | +/+ | | | |
| idh | −/− | −/− | −/− | −/− |
| ndh | +/+ | +/+ | | |
| nuo | +/+ | +/+ | | |
| pfk | −/+ | | | |
| pgi | +/+ | +/+ | | |
| pgk | −/− | −/− | −/− | −/− |
| pgl | +/+ | | | |
| pntAB | +/+ | +/+ | +/+ | +/+ |
| glk | +/+ | | | |
| ppc | ±/+ | −/+ | +/+ | +/+ |
| pta | | | | +/+ |
| pts | +/+ | | | |
| pyk | +/+ | | | |
| rpi | −/− | −/− | −/− | −/− |
| sdhABCD | +/+ | | | |
| tpi | −/+ | −/− | −/− | −/− |
| unc | +/+ | +/+ | | |
| zwf | +/+ | | | |
| sucAD | +/+ | | | |
| zwf, pnt | +/+ | | | |
| pck, mes | | | −/− | −/− |

TABLE 2-continued

Comparison of the predicted mutant growth characteristics from the gene deletion study to published experimental results with single and double mutants.

| Gene | Glucose (in vivo/in silico) | Glycerol (in vivo/in silico) | Succinate (in vivo/in silico) | Acetate (in vivo/in silico) |
|---|---|---|---|---|
| pck, pps | | | –/– | –/– |
| pgi, zwf | –/– | | | |
| pgi, gnd | –/– | | | |
| pta, acs | | | | –/– |
| tktA, tktB | –/– | | | |

Results are scored as + or – meaning growth or no growth determined from in vivo/in silico data. In 73 of 80 cases the in silico behavior is the same as the experimentally observed behavior.

What is claimed is:

1. A method performed in a computer of simulating a metabolic capability of an in silico strain of a microbe, comprising:
    obtaining a plurality of DNA sequences comprising most metabolic genes in a genome of the microbe to produce an in silico representation of a microbe;
    determining open reading frames of genes of unknown function in the microbe in said plurality of DNA sequences;
    assigning a potential function to proteins encoded by said open reading by determining the homology of said open reading frames to gene sequences encoding proteins of known function in a different organism;
    determining which of said open reading frames potentially correspond to metabolic genes by determining if the assigned function of said proteins is involved in cellular metabolism;
    determining substrates, products and stoichiometry of the reaction for each of the gene products of said metabolic genes having an assigned potential function;
    producing a genome specific stoichiometric matrix of said microbe produced by incorporating said substrates, products and stoichiometry into a stoichiometric matrix;
    determining a metabolic demand corresponding to a biomass composition of said microbe;
    calculating uptake rates of metabolites of said microbe;
    combining said metabolic demands and said uptake rates with said stoichiometric matrix to produce an in silico representation of said microbe;
    incorporating a general linear programming problem to produce an in silico strain of said microbe;
    performing a flux balance analysis on said in silico strain, and
    providing a visual output to a user of said analysis that simulates a metabolic capability of said strain predictive of said microbe's phenotype.

2. The method of claim 1, wherein said microbe is *Escherichia coli*.

3. The method of claim 1, wherein said genes involved in cellular metabolism comprise genes involved in central metabolism, amino acid metabolism, nucleotide metabolism, fatty acid metabolism, lipid metabolism, vitamin and cofactor biosynthesis, energy and redox generation or carbohydrate assimilation.

4. The method of claim 3, wherein said genes are involved in central metabolism.

5. The method of claim 3, wherein said genes are involved in amino acid metabolism.

6. The method of claim 3, wherein said genes are involved in nucleotide metabolism.

7. The method of claim 3, wherein said genes are involved in fatty acid metabolism.

8. The method of claim 3, wherein said genes are involved in lipid metabolism.

9. The method of claim 3, wherein said genes are involved in vitamin and cofactor biosynthesis.

10. The method of claim 3, wherein said genes are involved in energy and redox generation.

11. The method of claim 3, wherein said genes are involved in carbohydrate assimilation.

12. The method of claim 1, wherein assigning a function comprises performing a homology search using the Basic Local Alignment Search Tool (BLAST).

13. The method of claim 1, wherein said uptake rates are calculated by measuring the depletion of substrate from growth media of said microbe.

14. A method performed in a computer for simulating a metabolic capability of an in silico strain of a microbe, comprising:
    a) providing a nucleotide sequence of a potential metabolic gene in the microbe;
    b) determining substrates, products and stoichiometry of the reaction for the gene product of said potential metabolic gene, wherein said gene product having an unknown function in the microbe is assigned a potential function by determining homology of said nucleotide sequence to gene sequences encoding gene products of known function in a different organism;
    c) repeating steps a) and b) for most potential metabolic genes of said microbe to produce an in silico representation;
    d) producing a genome specific stoichiometric matrix produced by incorporating said substrates, products and stoichiometry of the potential metabolic gene products in said microbe into a stoichiometric matrix;
    e) determining a metabolic demand corresponding to a biomass composition of said microbe;
    f) calculating uptake rates of metabolites of said microbe;
    g) combining said metabolic demands and said uptake rates with said stoichiometric matrix to produce an in silico representation of said microbe;
    h) incorporating a general linear programming problem to produce an in silico strain of said microbe;
    i) performing a flux balance analysis on said in silico strain; and
    j) providing a visual output to a user of said analysis that simulates a metabolic capability of said strain predictive of said microbe's phenotype.

15. The method of claim 14, wherein the microbe is *Escherichia coli*.

16. The method of claim 14, wherein said metabolic gene is selected from the group consisting of: genes involved in central metabolism, amino acid metabolism, nucleotide metabolism, fatty acid metabolism, lipid metabolism, vitamin and cofactor biosynthesis, energy and redox generation and carbohydrate assimilation.

17. The method of claim 16, wherein said genes are involved in central metabolism.

18. The method of claim 16, wherein said genes are involved in amino acid metabolism.

19. The method of claim 16, wherein said genes are involved in nucleotide metabolism.

20. The method of claim 16, wherein said genes are involved in fatty acid metabolism.

21. The method of claim 16, wherein said genes are involved in lipid metabolism.

22. The method of claim 16, wherein said genes are involved in vitamin and cofactor biosynthesis.

23. The method of claim 16, wherein said genes are involved in energy and redox generation.

24. The method of claim 16, wherein said genes are involved in carbohydrate assimilation.

25. The method of claim 14, wherein assigning a function comprises performing a homology search using the Basic Local Alignment Search Tool (BLAST).

26. The method of claim 14, wherein said uptake rates are calculated by measuring the depletion of substrate from growth media of said microbe.

* * * * *